(12) United States Patent
Scott et al.

(10) Patent No.: US 11,871,935 B2
(45) Date of Patent: Jan. 16, 2024

(54) SURGICAL CLIP APPLIER WITH ARTICULATING JOINT PATH FOR SURGICAL CLIPS

(71) Applicant: Cilag GmbH International, Zug (CH)

(72) Inventors: Gregory Scott, Cincinnati, OH (US); Michael J. Stokes, Cincinnati, OH (US); Louise Emma van den Heuvel, Medford, MA (US); Kevin DelSignore, San Diego, CA (US); Cole Constantineau, Cambridge, MA (US)

(73) Assignee: Cilag GmbH International, Zug (CH)

( * ) Notice: Subject to any disclaimer, the term of this patent is extended or adjusted under 35 U.S.C. 154(b) by 461 days.

(21) Appl. No.: 17/087,897

(22) Filed: Nov. 3, 2020

(65) Prior Publication Data

US 2021/0169493 A1 Jun. 10, 2021

Related U.S. Application Data

(63) Continuation of application No. 15/897,282, filed on Feb. 15, 2018, now Pat. No. 10,820,910.

(51) Int. Cl.
| | | |
|---|---|---|
| *A61B 17/128* | (2006.01) | |
| *A61B 34/00* | (2016.01) | |
| *A61B 34/37* | (2016.01) | |
| *A61B 34/30* | (2016.01) | |
| *A61B 17/00* | (2006.01) | |

(52) U.S. Cl.
CPC .......... *A61B 17/1285* (2013.01); *A61B 34/30* (2016.02); *A61B 34/37* (2016.02); *A61B 34/71* (2016.02); *A61B 2017/00314* (2013.01); *A61B 2017/00323* (2013.01); *A61B 2017/00477* (2013.01)

(58) Field of Classification Search
CPC ......... A61B 34/00; A61B 34/30; A61B 34/37; A61B 17/00; A61B 17/1285; A61B 2017/00314; A61B 2017/00477; A61B 2017/00323; A61B 17/122; A61B 17/128
See application file for complete search history.

(56) References Cited

U.S. PATENT DOCUMENTS

| | | | |
|---|---|---|---|
| 5,474,566 A | * | 12/1995 | Alesi .................. A61B 17/1285 606/205 |
| 8,403,945 B2 | | 3/2013 | Whitfield et al. |

(Continued)

FOREIGN PATENT DOCUMENTS

| | | |
|---|---|---|
| EP | 0598529 A2 | 5/1994 |
| EP | 1468653 A2 | 10/2004 |

*Primary Examiner* — Vi X Nguyen
(74) *Attorney, Agent, or Firm* — Vorys, Sater, Seymour and Pease LLP

(57) ABSTRACT

A surgical clip applier includes a drive housing, an elongate shaft extending distally from the drive housing, and an end effector arranged at a distal end of the shaft. The end effector includes first and second jaw members, a cam slidably engageable with the first and second jaw members, and an actuation cable extending from the drive housing and operatively coupled to the cam. An articulation joint interposes the end effector and the shaft and includes a distal clevis coupled to the end effector, a proximal clevis coupled to a distal end of the shaft, and a spacer interposing the distal and proximal clevises. Longitudinal movement of the actuation cable moves the cam distally to collapse the first and jaw members.

14 Claims, 14 Drawing Sheets

(56) References Cited

U.S. PATENT DOCUMENTS

| | | |
|---|---|---|
| 9,232,979 B2 | 1/2016 | Parihar et al. |
| 2010/0106167 A1 | 4/2010 | Boulnois et al. |
| 2014/0005705 A1* | 1/2014 | Weir .................. A61B 18/08 |
| | | 606/169 |
| 2015/0073439 A1 | 3/2015 | Dannaher |
| 2016/0287252 A1 | 10/2016 | Parihar |
| 2017/0224351 A1 | 8/2017 | Khan |

* cited by examiner

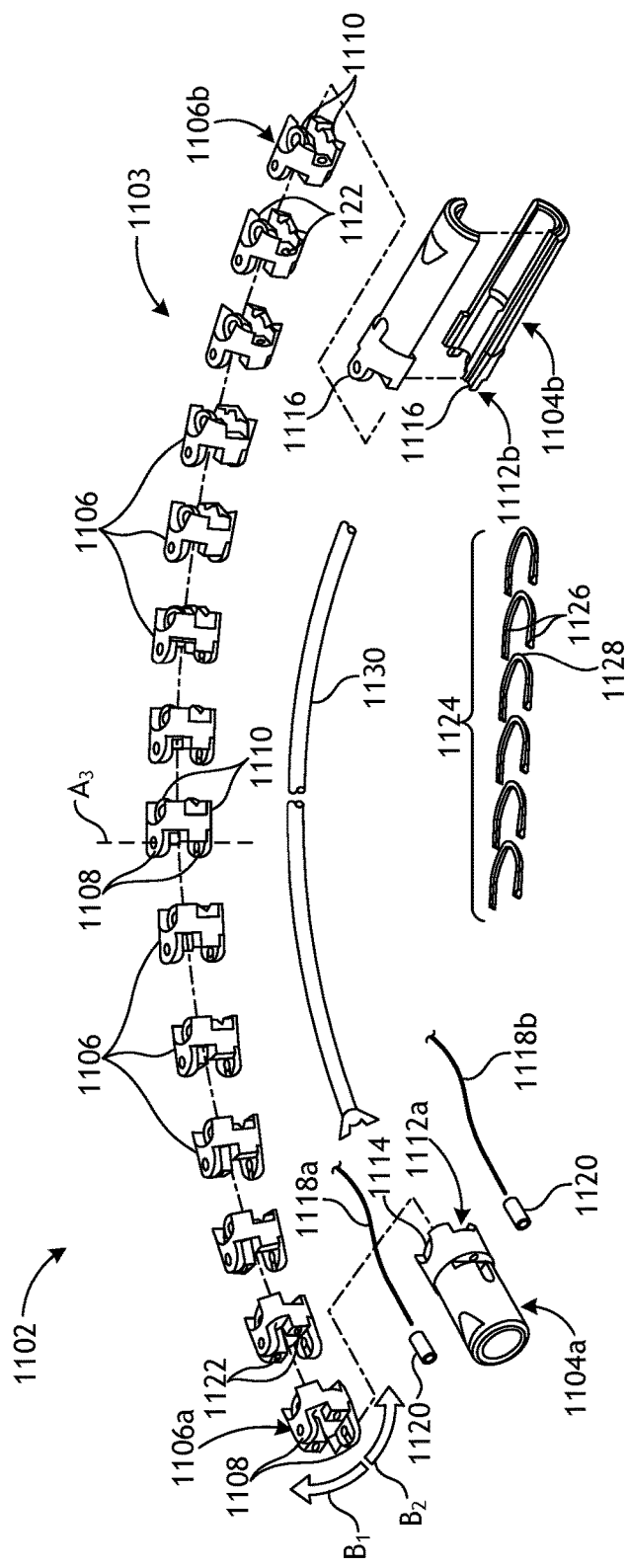
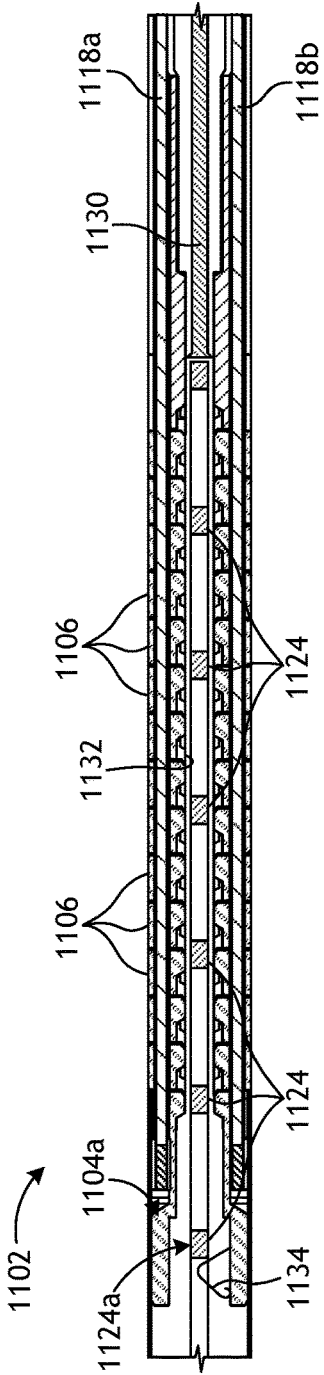
FIG. 11B
FIG. 11C

SURGICAL CLIP APPLIER WITH ARTICULATING JOINT PATH FOR SURGICAL CLIPS

BACKGROUND

Minimally invasive surgical (MIS) tools and procedures are often preferred over traditional open surgical approaches due to their propensity toward reducing post-operative recovery time and leaving minimal scarring. Endoscopic surgery is one type of MIS procedure in which a surgical tool operably connected to an elongate shaft is introduced into the body of a patient through a natural bodily orifice. Laparoscopic surgery is a related type of MIS procedure in which a small incision is formed in the abdomen of a patient and a trocar is inserted through the incision to form a surgical access pathway for a surgical tool and elongate shaft. Once located within the abdomen, the surgical tool engages and/or treats tissue in a number of ways to achieve a diagnostic or therapeutic effect. Manipulation and engagement of the surgical tool may take place via various components passing through the elongate shaft.

One surgical instrument commonly used with a trocar is a surgical clip applier, which can be used to ligate blood vessels, ducts, shunts, or portions of body tissue during surgery. Traditional surgical clip appliers have a handle and an elongate shaft extending from the handle. A pair of movable opposed jaws is positioned at the end of the elongate shaft for holding and forming a surgical clip or "ligation clip" therebetween. In operation, a user (e.g., a surgeon or clinician) positions the jaws around the vessel or duct and squeezes a trigger on the handle to close the jaws and thereby collapse the surgical clip over the vessel.

More recently, however, robotic systems have been developed to assist in MIS procedures. Instead of directly engaging a surgical instrument, users are now able to manipulate and engage surgical instruments via an electronic interface communicatively coupled to a robotic manipulator. With the advances of robotic surgery, a user need not even be in the operating room with the patient during the surgery.

Robotic surgical systems are also now capable of utilizing robotically controlled clip appliers. Such clip appliers include features for robotically feeding and forming surgical clips. Advances and improvements to the methods and devices for applying surgical clips to vessels, ducts, shunts, etc. is continuously in demand to make the process more efficient and safe.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 11B is an exploded view of the articulation joint of FIG. 11A.

FIG. 11C is a cross-sectional side view of the assembled articulation joint of FIG. 11A in an unarticulated state.

DETAILED DESCRIPTION

The present disclosure is related to surgical systems and, more particularly, to surgical clip appliers having an articulation joint made up of a flexible shaft length that feeds surgical clips therethrough and to jaws for crimping.

Embodiments discussed herein describe improvements to articulable surgical clip appliers. The surgical clip appliers described herein may include a drive housing, an elongate shaft that extends distally from the drive housing, an end effector arranged at a distal end of the elongate shaft and including first and second jaw members. An articulation joint may interpose the end effector and the elongate shaft, and may comprise a flexible shaft length articulable in a plane of motion. A lumen is defined within the flexible shaft length and extends between the ends of the flexible shaft length. A clip track is provided within the lumen and extending at least partially between the ends to guide surgical clips through the articulation joint. The clip track may be configured to positively engage the surgical clips throughout the path, and the surgical clips may be able to slidably translate through the articulation joint without bending or pre-forming.

Figure 1:
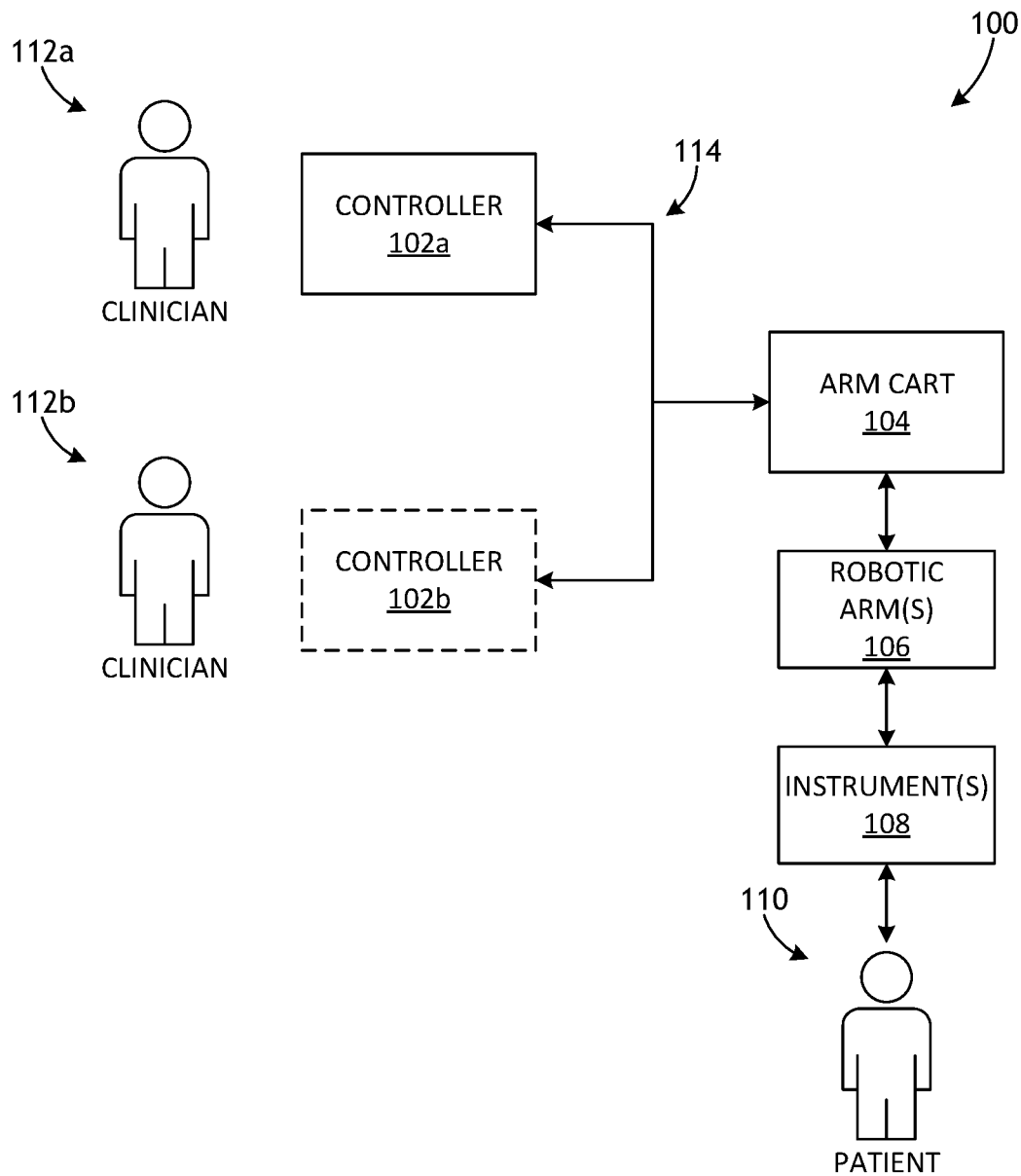
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102*a* and at least one arm cart 104. The arm cart 104 may be mechanically and/or electrically coupled to a robotic manipulator and, more particularly, to one or more robotic arms 106 or "tool drivers". Each robotic arm 106 may include and otherwise provide a location for mounting one or more surgical tools or instruments 108 for performing various surgical tasks on a patient 110. Operation of the robotic arms 106 and instruments 108 may be directed by a clinician 112a (e.g., a surgeon) from the master controller 102a.

In some embodiments, a second master controller 102b (shown in dashed lines) operated by a second clinician 112b may also direct operation of the robotic arms 106 and instruments 108 in conjunction with the first clinician 112a. In such embodiments, for example, each clinician 102a,b may control different robotic arms 106 or, in some cases, complete control of the robotic arms 106 may be passed between the clinicians 102a,b. In some embodiments, additional arm carts (not shown) having additional robotic arms (not shown) may be utilized during surgery on a patient 110, and these additional robotic arms may be controlled by one or more of the master controllers 102a,b.

The arm cart 104 and the master controllers 102a,b may be in communication with one another via a communications link 114, which may be any type of wired or wireless telecommunications means configured to carry a variety of communication signals (e.g., electrical, optical, infrared, etc.) according to any communications protocol.

The master controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical instrument(s) 108, for example, for opening and closing opposing jaws, applying an electrical potential (current) to an electrode, or the like. The master controllers 102a,b can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand the various embodiments and forms of the various embodiments of robotic surgery apparatus, systems, and methods disclosed herein.

Figure 2:
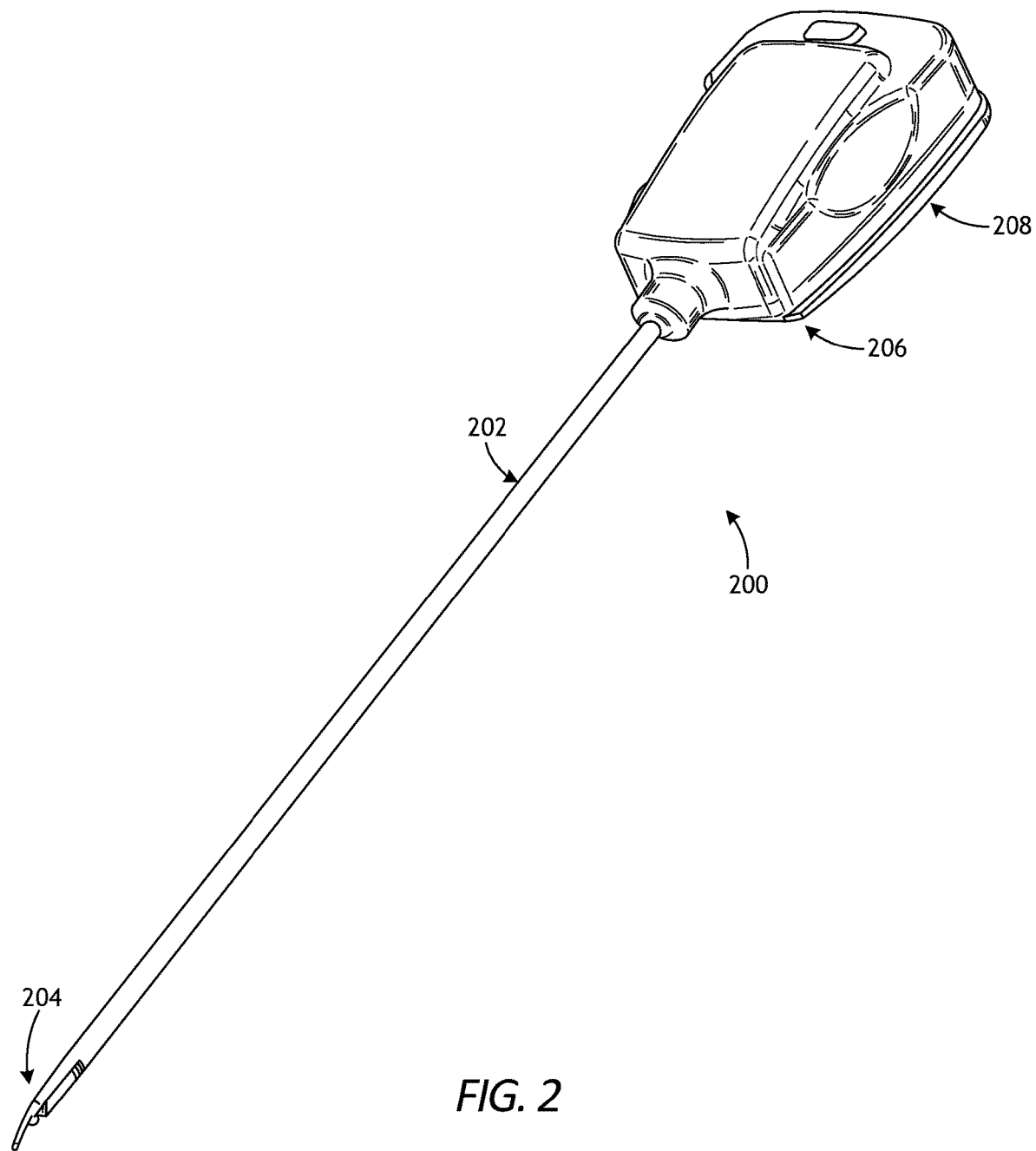
FIG. 2 is an isometric top view of an example surgical tool that may incorporate some or all of the principles of the present disclosure.

FIG. 2 is an isometric top view of an example surgical tool 200 that may incorporate some or all of the principles of the present disclosure. The surgical tool 200 may be the same as or similar to the surgical instrument(s) 108 of FIG. 1 and, therefore, may be used in conjunction with the robotic surgical system 100 of FIG. 1. Accordingly, the surgical tool 200 may be designed to be releasably coupled to a robotic arm 106 (FIG. 1) of a robotic manipulator of the robotic surgical system 100. Full detail and operational description of the surgical tool 200 is provided in U.S. Patent Pub. 2016/0287252, entitled "Clip Applier Adapted for Use with a Surgical Robot," the contents of which are hereby incorporated by reference in their entirety.

While the surgical tool 200 is described herein with reference to a robotic surgical system, it is noted that the principles of the present disclosure are equally applicable to non-robotic surgical tools or, more specifically, manually operated surgical tools. Accordingly, the discussion provided herein relating to robotic surgical systems merely encompasses one example application of the presently disclosed inventive concepts.

As illustrated, the surgical tool 200 can include an elongate shaft 202, an end effector 204 coupled to the distal end of the shaft 202, and a drive housing 206 coupled to the proximal end of the shaft 202. The terms "proximal" and "distal" are defined herein relative to a robotic surgical system having an interface configured to mechanically and electrically couple the surgical tool 200 (e.g., the drive housing 206) to a robotic manipulator. The term "proximal" refers to the position of an element closer to the robotic manipulator and the term "distal" refers to the position of an element closer to the end effector 204 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

In applications where the surgical tool 200 is used in conjunction with a robotic surgical system (e.g., system 100 of FIG. 1), the drive housing 206 can include a tool mounting portion 208 designed with features that releasably couple the surgical tool 200 to a robotic arm (e.g., the robotic arms 106 or "tool drivers" of FIG. 1) of a robotic manipulator. The tool mounting portion 208 may releasably attach (couple) the drive housing 206 to a tool driver in a variety of ways, such as by clamping thereto, clipping thereto, or slidably mating therewith. In some embodiments, the tool mounting portion 208 may include an array of electrical connecting pins, which may be coupled to an electrical connection on the mounting surface of the tool driver. While the tool mounting portion 208 is described herein with reference to mechanical, electrical, and magnetic coupling elements, it should be understood that a wide variety of telemetry modalities might be used, including infrared, inductive coupling, or the like.

Figure 3:
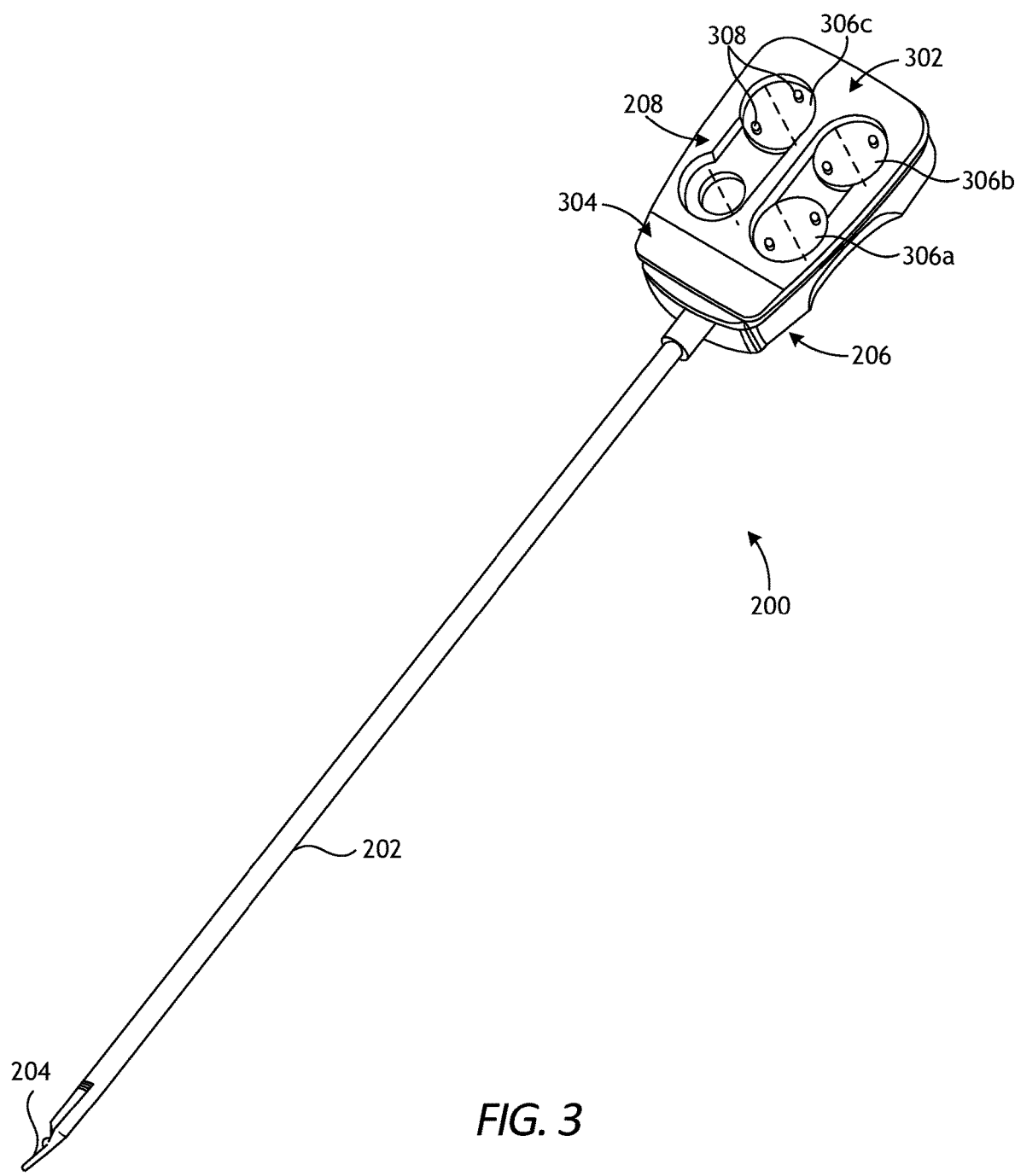
FIG. 3 is an isometric bottom view of the surgical tool of FIG. 2.

FIG. 3 is an isometric bottom view of the surgical tool 200. The surgical tool 200 further includes an interface 302 that mechanically and electrically couples the tool mounting portion 208 to a robotic manipulator. In various embodiments, the tool mounting portion 208 includes a tool mounting plate 304 that operably supports a plurality of drive inputs, shown as a first drive input 306a, a second drive input 306b, and a third drive input 306c. While only three drive inputs 306a-c are shown in FIG. 3, more or less than three may be employed, without departing from the scope of the disclosure.

In the illustrated embodiment, each drive input 306a-c comprises a rotatable disc configured to align with and couple to a corresponding input actuator (not shown) of a given tool driver. Moreover, each drive input 306a-c provides or defines one or more surface features 308 configured to align with mating surface features provided on the corresponding input actuator. The surface features 308 can include, for example, various protrusions and/or indentations that facilitate a mating engagement.

Figure 4:
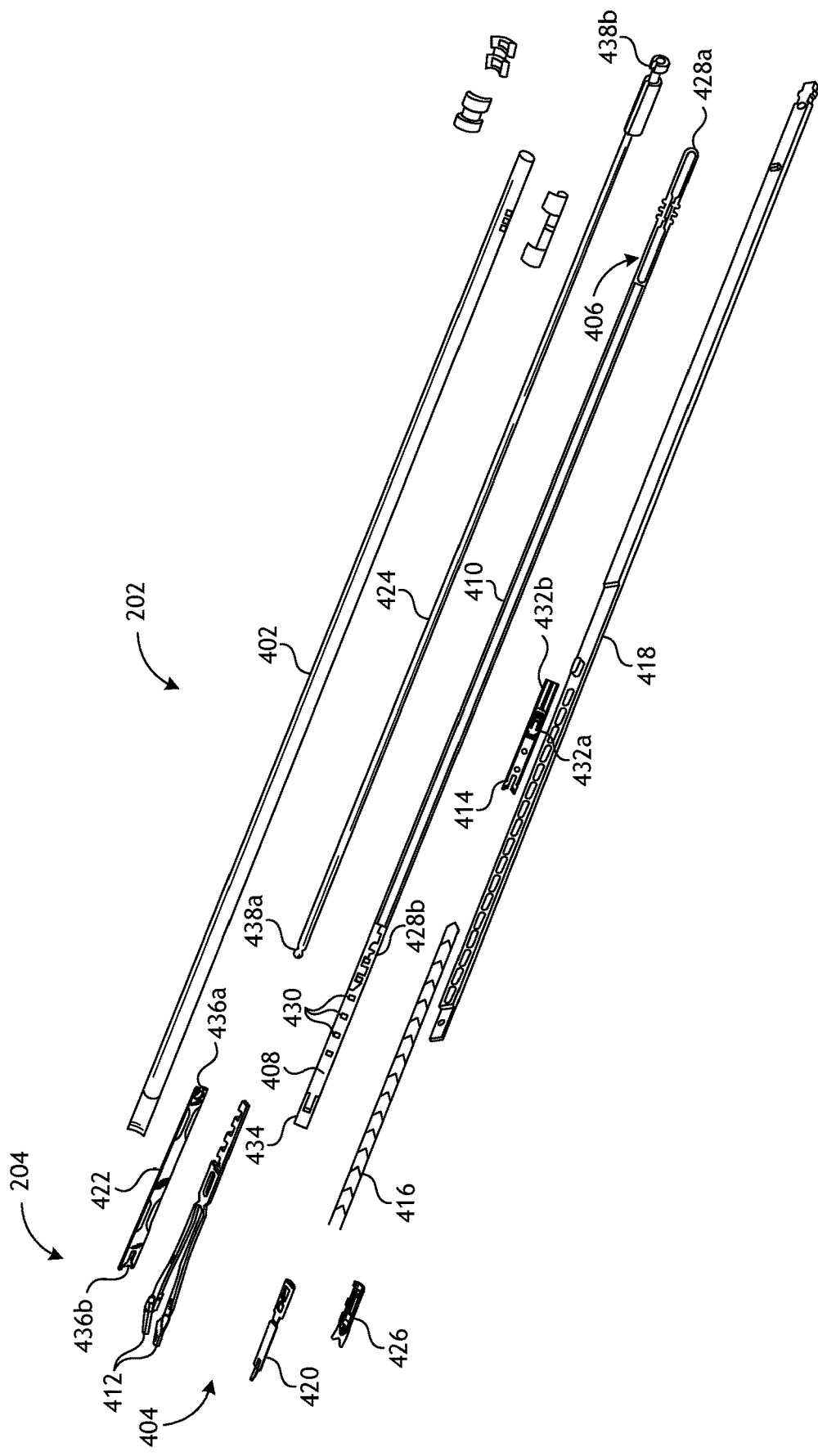
FIG. 4 is an exploded view of the elongate shaft and the end effector of the surgical tool of FIGS. 2 and 3.

FIG. 4 is an exploded view of one example of the elongate shaft 202 and the end effector 204 of the surgical tool 200 of FIGS. 2 and 3, according to one or more embodiments. As illustrated, the shaft 202 includes an outer tube 402 that houses the various components of the shaft 202, which can include a jaw retaining assembly 404. The jaw retaining assembly 404 includes a jaw retainer shaft 406 with a clip track 408 and a push rod channel 410 formed thereon. The end effector 204 includes opposing jaws 412 that are configured to mate to a distal end of the clip track 408.

The shaft 202 also includes a clip advancing assembly, which, in one example embodiment, can include a feeder shoe 414 adapted to be slidably disposed within the clip track 408. The feeder shoe 414 is designed to advance a series of clips 416 positioned within the clip track 408, and a feedbar 418 is adapted to drive the feeder shoe 414 through the clip track 408. An advancer assembly 420 is adapted to mate to a distal end of the feedbar 418 for advancing a distal-most clip into the jaws 412.

The shaft 202 furthers include a clip forming or camming assembly operable to collapse the jaws 412 and thereby crimp (crush) a surgical clip 416 positioned between (interposing) the jaws 412. The camming assembly includes a cam 422 that slidably mates to the jaws 412, and a push rod 424 that moves the cam 422 relative to the jaws 412 to collapse the jaws 412. A tissue stop 426 can mate to a distal end of the clip track 408 to help position the jaws 412 relative to a surgical site.

The jaw retainer shaft 406 is extendable within and couples to the outer tube 402 at a proximal end 428a, and its distal end 428b is adapted to mate with the jaws 412. The push rod channel 410 formed on the jaw retainer shaft 406 may be configured to slidably receive the push rod 424, which is used to advance the cam 422 over the jaws 412. The clip track 408 extends distally beyond the distal end 428b of the jaw retainer shaft 406 to allow a distal end of the clip track 408 to be substantially aligned with the jaws 412.

The clip track 408 can include several openings 430 formed therein for receiving an upper or "superior" tang 432a formed on the feeder shoe 414 adapted to be disposed within the clip track 408. The clip track 408 can also include a stop tang 434 formed thereon that is effective to be engaged by a corresponding stop tang formed on the feeder shoe 414 to prevent movement of the feeder shoe 414 beyond a distal-most position. To facilitate proximal movement of the feeder shoe 414 within the clip track 408, the feeder shoe 414 can also include a lower or "inferior" tang 432b formed on the underside thereof for allowing the feeder shoe 414 to be engaged by the feedbar 418 as the feedbar 418 is moved distally. In use, each time the feedbar 418 is moved distally, a detent formed in the feedbar 418 engages the inferior tang 432b and moves the feeder shoe 414 distally a predetermined distance within the clip track 408. The feedbar 418 can then be moved proximally to return to its initial position, and the angle of the inferior tang 432b allows the inferior tang 432b to slide into the next detent formed in the feedbar 418.

The jaws 412 include first and second opposed jaw members that are movable (collapsible) relative to one another and are configured to receive a surgical clip from the series of clips 416 therebetween. The jaw members can each include a groove formed on opposed inner surfaces thereof for receiving the legs of a surgical clip 416 in alignment with the jaw members. In the illustrated embodiment, the jaw members are biased to an open position and a force is required to urge the jaw members toward one another to crimp the interposing clip 416. The jaw members can also each include a cam track formed thereon for allowing the cam 422 to slidably engage and move the jaw members toward one another. A proximal end 436a of the cam 422 is matable with a distal end 438a of the push rod 424, and a distal end 436b of the cam 422 is adapted to engage and actuate the jaws 412. The proximal end 438b of the push rod 424 is matable with a closure link assembly associated with the drive housing 206 for moving the push rod 424 and the cam 422 relative to the jaws 412.

The distal end 436b of the cam 422 includes a camming channel or tapering recess formed therein for slidably receiving corresponding cam tracks provided by the jaw members. In operation, the cam 422 is advanced from a proximal position, in which the jaw members are spaced apart from one another, to a distal position, where the jaw members are collapsed to a closed position. As the cam 422 is advanced over the jaw members, the tapering recess at the distal end 436b serves to push the jaw members toward one another, thereby crimping a surgical clip 416 disposed therebetween.

Figure 5:
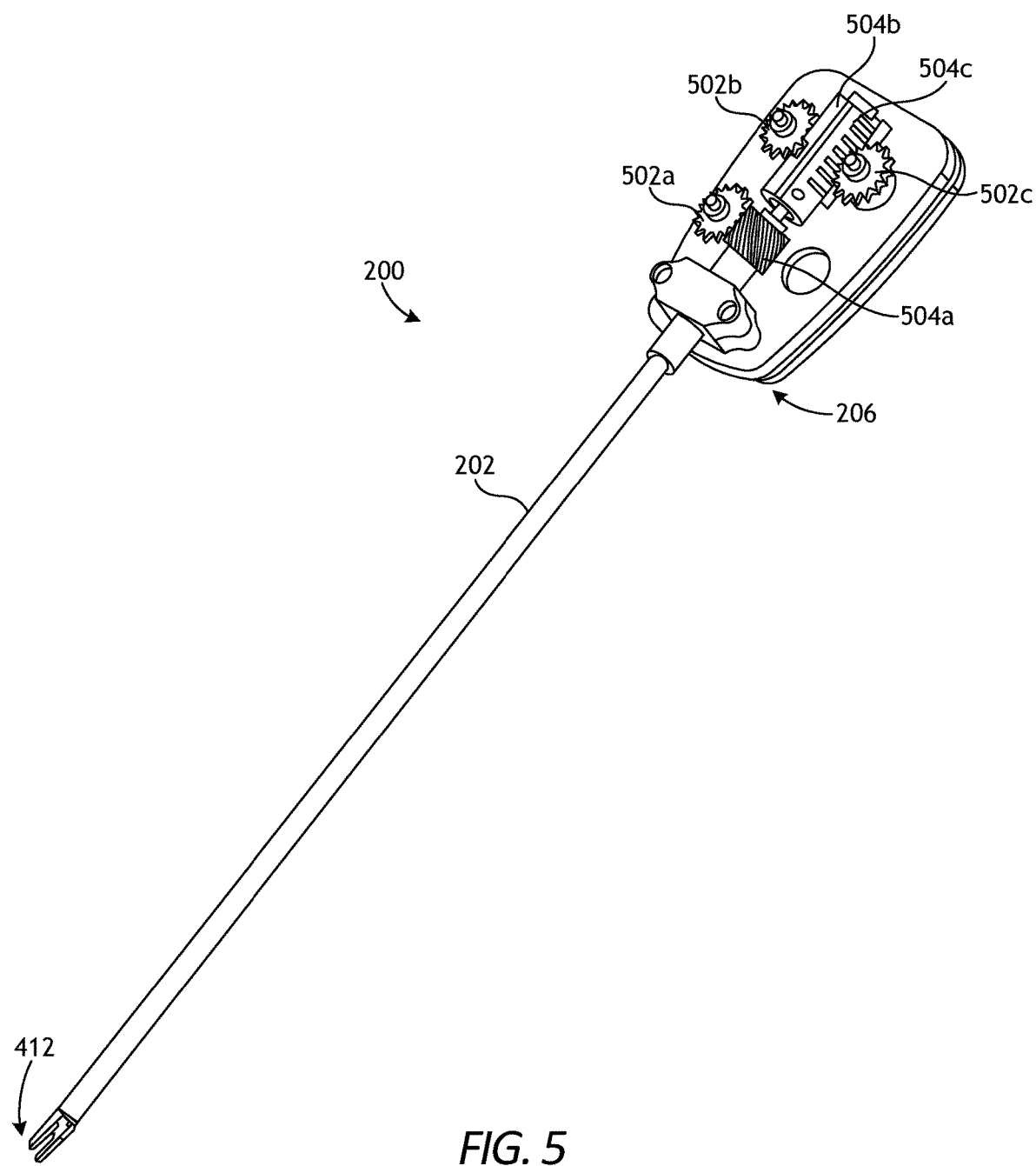
FIG. 5 is an exposed isometric view of the surgical tool of FIG. 2.

FIG. 5 is an exposed isometric view of the surgical tool 200 of FIG. 2, according to one or more embodiments. The shroud or covering of the drive housing 206 has been removed to reveal the internal component parts. As illustrated, the surgical tool 200 may include a first drive gear 502a, a second drive gear 502b, and a third drive gear 502c. The first drive gear 502a may be operatively coupled to (or extend from) the first drive input 306a (FIG. 3) such that actuation of the first drive input 306a correspondingly rotates the first drive gear 502a. Similarly, the second and third drive gears 502b,c may be operatively coupled to (or extend from) the second and third drive inputs 306b,c (FIG. 3), respectively, such that actuation of the second and third drive inputs 306b,c correspondingly rotates the second and third drive gears 502b,c, respectively.

The first drive gear 502a may be configured to intermesh with a first driven gear 504a, which is operatively coupled to the shaft 202. In the illustrated embodiment, the driven gear 504a comprises a helical gear. In operation, rotation of the first drive gear 502a about a first axis correspondingly rotates the first driven gear 504a about a second axis orthogonal to the first axis to control rotation of the shaft 202 in clockwise and counter-clockwise directions based on the rotational direction of the first drive gear 502a.

The second drive gear 502b may be configured to intermesh with a second driven gear 504b (partially visible in FIG. 5), and the third drive gear 502c may be configured to intermesh with a third driven gear 504c. In the illustrated embodiment, the second and third drive and driven gears 502b,c, 504b,c comprise corresponding rack and pinion interfaces, where the driven gears 504b,c comprise the rack and the drive gears 502b,c comprise the pinion. Independent rotation of the second and third drive gears 502b,c will cause the second and third driven gears 504b,c, respectively, to translate linearly relative to (independent of) one another.

In at least one embodiment, actuation (rotation) of the third drive gear 502c will result in a surgical clip 416 (FIG. 4) being fed into the jaws 412. More particularly, the third driven gear 504c may be operatively coupled to the feedbar 418 (FIG. 4) and, upon rotation of the third drive gear 502c in a first angular direction, the third driven gear 504c will advance distally and correspondingly advance the feedbar 418 a sufficient distance to fully advance a surgical clip into the jaws 412. Rotation of the third drive gear 502c may be precisely controlled by an electrical and software interface to deliver the exact linear travel to the third driven gear 504c necessary to feed a clip 416 into the jaws 412.

Upon delivery of a clip into the jaws 412, or after a predetermined amount of rotation of the third drive gear 502c, rotation of the third drive gear 502c is reversed in a second angular direction to move the third driven gear 504c linearly in a proximal direction, which correspondingly moves the feedbar 418 proximally. This process may be repeated several times to accommodate a predetermined number of clips residing in the shaft 202.

Actuation of the second drive gear 502b causes the jaws 412 to close or collapse to crimp a surgical clip. More particularly, the second driven gear 504b may be coupled to the proximal end 438b (FIG. 4) of the push rod 424 (FIG. 4) and, upon actuation of the second drive gear 502b in a first angular direction, the second driven gear 504b will be advanced linearly in a distal direction and correspondingly drive the push rod 424 distally, which drives the cam 422 over the jaws 412 to collapse the jaw members and crimp a surgical clip positioned in the jaws 412. Once a surgical clip is successfully deployed, rotation of the second drive gear 502b is reversed in the opposite angular direction to move the second driven gear 504b in a proximal direction, which correspondingly moves the push rod 424 and the cam 422 proximally and permits the jaws 412 to open once again.

The processes of delivering a surgical clip into the jaws 412 and collapsing the jaws 412 to crimp the surgical clip are not limited to the actuation mechanisms and structures described herein. In alternative embodiments, for example, the second and third driven gears 504b,c may instead comprise capstan pulleys configured to route and translate drive cables within the shaft 202. In such embodiments, the drive cables may be operatively coupled to one or more lead screws or other types of rotating members positioned within the shaft 202 near the distal end and capable of advancing the feedbar 418 to deliver a surgical clip into the jaws 412 and advancing the cam 422 to collapse the jaws 412 and crimp the surgical clip.

Figure 6:
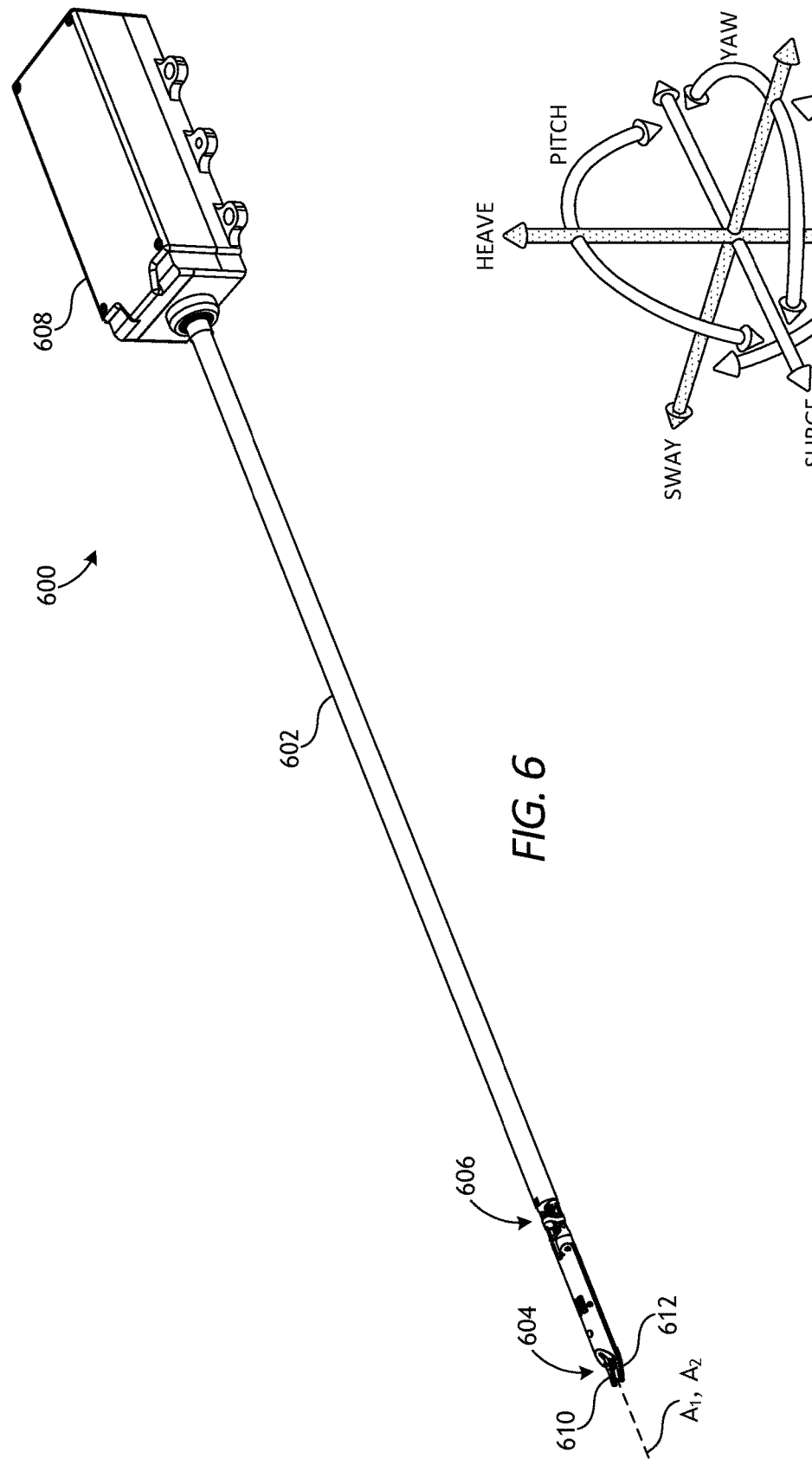
FIG. 6 is a side view of an example surgical tool that may incorporate some or all of the principles of the present disclosure.

FIG. 6 is an isometric top view of another example surgical tool 600 that may incorporate some or all of the principles of the present disclosure. Similar to the surgical tool 200 of FIG. 2, the surgical tool 600 may be used in conjunction with the robotic surgical system 100 of FIG. 1. As illustrated, the surgical tool 600 includes an elongate shaft 602, an end effector 604 positioned at the distal end of the shaft 602, an articulation joint 606 (alternately referred to as a "articulable wrist joint") that couples the end effector 604 to the distal end of the shaft 602, and a drive housing 608 coupled to the proximal end of the shaft 602. In some embodiments, the shaft 602, and hence the end effector 604 coupled thereto, is configured to rotate about a longitudinal axis $A_1$.

In the illustrated embodiment, the end effector 604 comprises a clip applier that includes opposing jaw members 610, 612 configured to collapse toward one another to crimp a surgical clip. The articulation joint 606 facilitates pivoting movement of the end effector 604 relative to the shaft 602 to position the end effector 604 at desired orientations and locations relative to a surgical site. The housing 608 includes (contains) various actuation mechanisms designed to control articulation at the articulation joint 606 and operation of the end effector 604.

Figure 7:
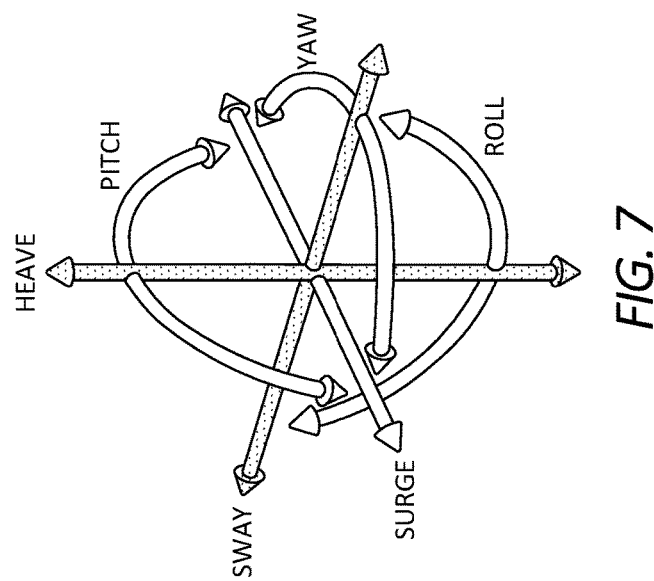
FIG. 7 illustrates potential degrees of freedom in which the wrist of FIG. 1 may be able to articulate (pivot).

FIG. 7 illustrates the potential degrees of freedom in which the articulation joint 606 may be able to articulate (pivot). The degrees of freedom of the articulation joint 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the articulation joint 606 (e.g., X-axis), yaw movement about a second axis of the articulation joint 606 (e.g., Y-axis), and combinations thereof to allow for 360° rotational movement of the end effector 604 about the articulation joint 606. In other applications, the pivoting motion can be limited to movement in a single plane, e.g., only pitch movement about the first axis of the articulation joint 606 or only yaw movement about the second axis of the articulation joint 606, such that the end effector 604 moves only in a single plane.

Referring again to FIG. 6, the surgical tool 600 includes a plurality of drive cables (generally obscured in FIG. 6) that form part of a cable driven motion system configured to facilitate operation and articulation (movement) of the end effector 604 relative to the shaft 602. For example, selectively moving the drive cables can actuate the end effector 604 and thereby collapse the jaw members 610, 612 toward each other. Moreover, moving the drive cables can also move the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. In the articulated position, the longitudinal axes $A_1, A_2$ would be angularly offset from each other such that the end effector 604 is at a non-zero angle relative to the shaft 602.

Figure 8:
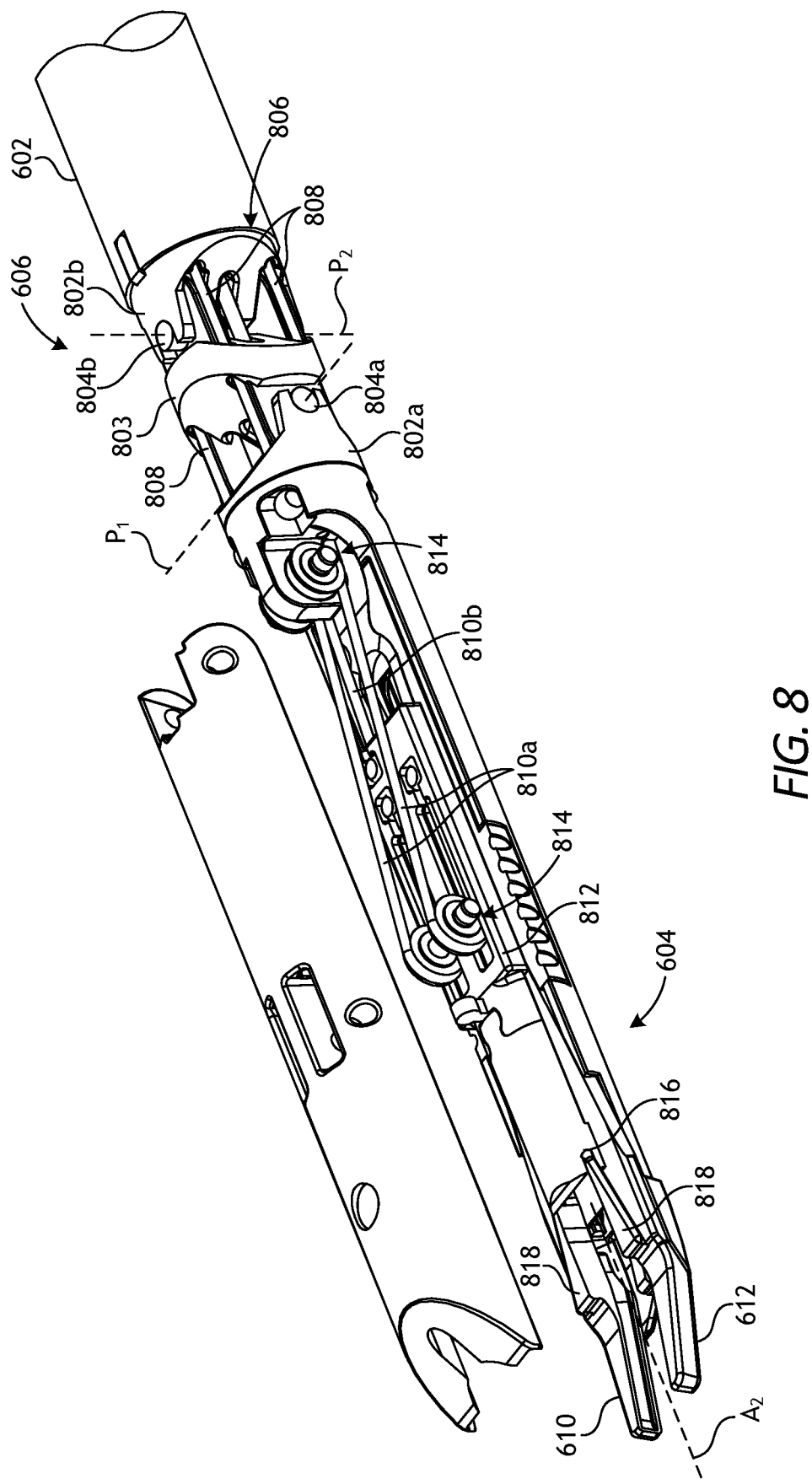
FIG. 8 is an enlarged isometric view of the distal end of the surgical tool of FIG. 6.

FIG. 8 is an enlarged isometric view of the distal end of the surgical tool 600 of FIG. 6. More specifically, FIG. 8 depicts an enlarged and partially exploded view of the end effector 604 and the articulation joint 606. The articulation joint 606 operatively couples the end effector 604 to the shaft 602. To accomplish this, the articulation joint 606 includes a distal clevis 802a, a proximal clevis 802b, and a spacer 803 interposing the distal and proximal clevises 802a,b. The end effector 604 is coupled to the distal clevis 802a and the distal clevis 802a is rotatably mounted to the spacer 803 at a first axle 804a. The spacer 803 is rotatably mounted to the proximal clevis 802b at a second axle 804b and the proximal clevis 802b is coupled to a distal end 806 of the shaft 602.

The articulation joint 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 604, and movement about the second pivot axis $P_2$ provides "pitch" articulation of the end effector 604.

A plurality of drive cables 808 extend longitudinally within the shaft 602 and pass through the wrist 106 to be operatively coupled to the end effector 604. The drive cables 808 form part of the cable driven motion system briefly described above, and may be referred to and otherwise characterized as cables, bands, lines, cords, wires, ropes, strings, twisted strings, elongate members, etc. The drive cables 808 can be made from a variety of materials including, but not limited to, metal (e.g., tungsten, stainless steel, etc.) or a polymer.

The drive cables 808 extend proximally from the end effector 604 to the drive housing 608 (FIG. 6) where they are operatively coupled to various actuation mechanisms or devices housed (contained) therein to facilitate longitudinal movement (translation) of the drive cables 808. Selective actuation of the drive cables 808 causes the end effector 604 to articulate (pivot) relative to the shaft 602. Moving a given drive cable 808 constitutes applying tension (i.e., pull force) to the given drive cable 808 in a proximal direction, which causes the given drive cable 808 to translate and thereby cause the end effector 604 to move (articulate) relative to the shaft 602.

One or more actuation cables 810, shown as first actuation cables 810a and second actuation cables 810b, may also extend longitudinally within the shaft 602 and pass through the wrist 106 to be operatively coupled to the end effector 604. The actuation cables 810a,b may be similar to the drive cables 808 and also form part of the cable driven motion system. Selectively actuating the actuation cables 810a,b causes the end effector 604 to actuate, such as collapsing the first and second jaw members 610, 612 to crimp a surgical clip (not shown).

More specifically, the actuation cables 810a,b may be operatively coupled to a cam 812 that is slidably engageable with the jaw members 610, 612. One or more pulleys 814 may be used to receive and redirect the first actuation cables 810a for engagement with the cam 812. Longitudinal movement of the first actuation cables 810a correspondingly moves the cam 812 distally relative to the jaw members 610, 612. The distal end of the cam 812 includes a tapering recess or camming channel 816 formed therein for slidably receiving corresponding cam tracks 818 provided by the jaw members 610, 612. As the cam 812 is advanced distally, the camming channel 816 pushes (collapses) the jaw members 610, 612 toward one another, thereby crimping a surgical clip (not shown) disposed therebetween. Actuation of the second actuation cables 810b (one shown) pulls the cam 812 proximally, thereby allowing the jaw members 610, 612 to open again to receive another surgical clip.

Although not expressly depicted in FIG. 8, an assembly including, for example, a feedbar, a feeder shoe, and a clip track may be included at or near the end effector 604 to facilitate feeding surgical clips into the jaw members 610, 612. In some embodiments, the feedbar (or a connecting member) may be flexible and extend through the articulation joint 606.

Figure 9:
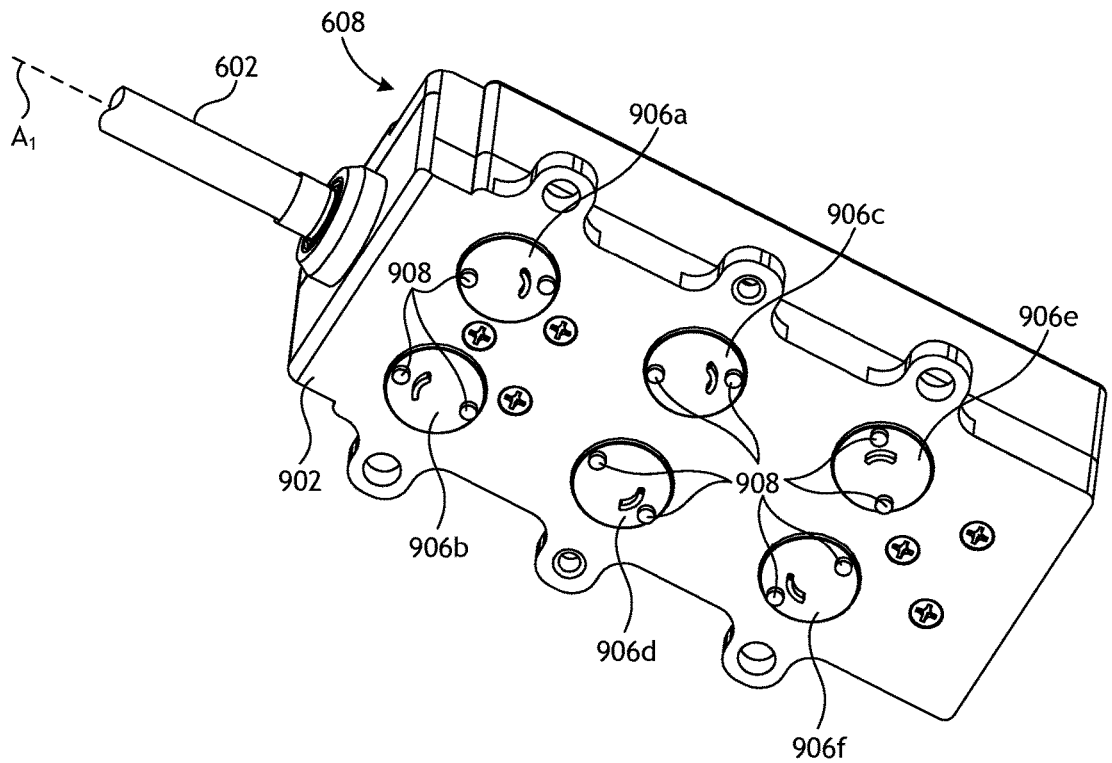
FIG. 9 is a bottom view of the drive housing of the surgical tool of FIG. 6.

FIG. 9 is a bottom view of the drive housing 608, according to one or more embodiments. As illustrated, the drive housing 608 may include a tool mounting interface 902 used to operatively couple the drive housing 608 to a tool driver of a robotic manipulator. The tool mounting interface 902 may mechanically, magnetically, and/or electrically couple the drive housing 608 to a tool driver.

As illustrated, the interface 902 includes and supports a plurality of drive inputs, shown as drive inputs 906a, 906b, 906c, 906d, 906e, and 906f. Each drive input 906a-f may comprise a rotatable disc configured to align with and couple to a corresponding input actuator (not shown) of a tool driver. Moreover, each drive input 906a-f provides or defines one or more surface features 908 configured to align with mating features provided on the corresponding input actuator. The surface features 908 can include, for example, various protrusions and/or indentations that facilitate a mating engagement.

In some embodiments, actuation of the first drive input 906a may control rotation of the elongate shaft 602 about its longitudinal axis $A_1$. Depending on the rotational actuation of the first drive input 906a, the elongate shaft 602 may be rotated clockwise or counter-clockwise. In some embodiments, selective actuation of the second and third drive inputs 906b,c may cause movement (axial translation) of the actuation cables 810a,b (FIG. 8), which causes the cam 812 (FIG. 8) to move and crimp a surgical clip, as generally described above. In some embodiments, actuation of the fourth drive input 906d feeds a surgical clip into the jaw members 610, 612 (FIG. 8). In some embodiments, actuation of the fifth and sixth drive inputs 906e,f causes movement (axial translation) of the drive cables 808 (FIG. 8), which results in articulation of the end effector 604. Each of the drive inputs 906a-f may be actuated based on user inputs communicated to a tool driver coupled to the interface 902, and the user inputs may be received via a computer system incorporated into the robotic surgical system.

Figure 10:
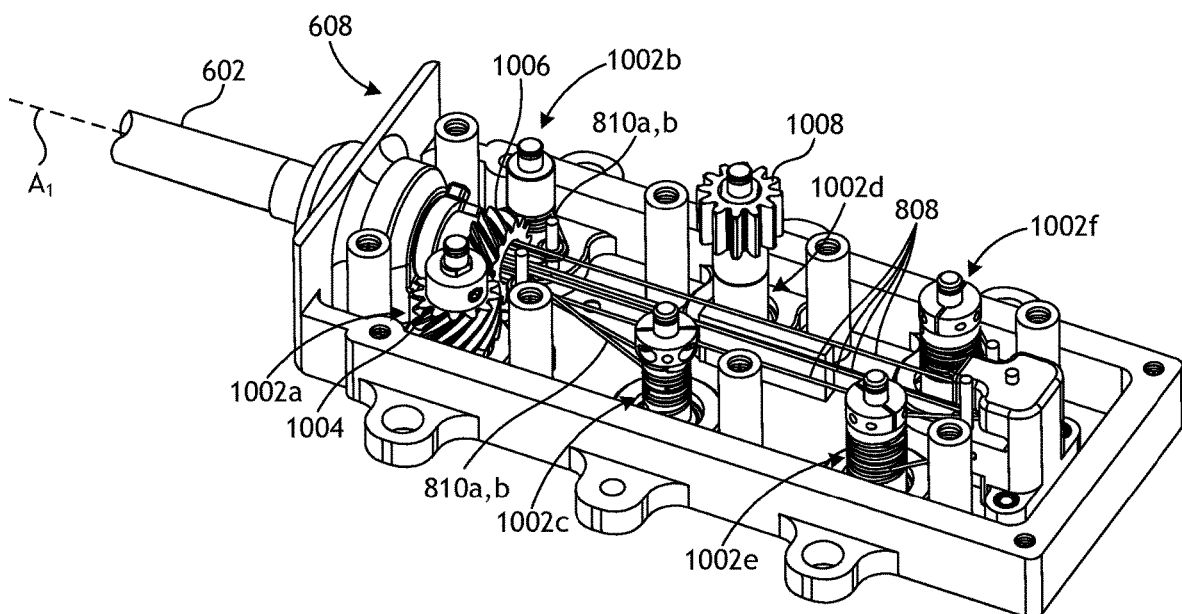
FIG. 10 is an isometric exposed view of the interior of the drive housing of the surgical tool of FIG. 6.

FIG. 10 is an isometric exposed view of the interior of the drive housing 608, according to one or more embodiments. Several component parts that may otherwise be contained within the drive housing 608 are not shown in FIG. 10 to enable discussion of the depicted component parts.

As illustrated, the drive housing 608 contains a first capstan 1002a, which is operatively coupled to or extends from the first drive input 906a (FIG. 9) such that actuation of the first drive input 906a results in rotation of the first capstan 1002a. A helical drive gear 1004 is coupled to or forms part of the first capstan 1002a and is configured to mesh and interact with a driven gear 1006 operatively coupled to the shaft 602 such that rotation of the driven gear 1006 correspondingly rotates the shaft 602. Accordingly, rotation of the helical drive gear 1004 (via actuation of the first drive input 906a of FIG. 9) will drive the driven gear 1006 and thereby control rotation of the elongate shaft 602 about the longitudinal axis $A_1$.

The drive housing 608 also includes second and third capstans 1002b and 1002c operatively coupled to or extending from the second and third drive inputs 906b,c (FIG. 9), respectively, such that actuation of the second and third drive inputs 906b,c results in rotation of the second and third capstans 1002b,c. The second and third capstans 1002b,c comprise capstan pulleys operatively coupled to the actuation cables 810a,b (FIG. 8) such that rotation of a given capstan 1002b,c actuates (longitudinally moves) a corresponding one of the actuation cables 810a,b. Accordingly, selective rotation of the second and third capstans 1002b,c via actuation of the second and third drive inputs 906b,c, respectively, will cause movement (axial translation) of the actuation cables 810a,b, which causes the cam 812 (FIG. 8) to move and crimp a surgical clip.

The drive housing 608 further includes a fourth capstan 1002d, which is operatively coupled to or extends from the fourth drive input 906d (FIG. 9) such that actuation of the fourth drive input 906d results in rotation of the fourth capstan 1002d. A spur gear 1008 is coupled to or forms part of the fourth capstan 1002d and is configured to mesh and interact with a rack gear (not shown) also contained within the drive housing 608. The rack gear may be operatively coupled to a feedbar (or another connecting member) which facilitates operation of a feeder shoe and associated clip track to feed surgical clips into the jaw members 610, 612 (FIGS. 6 and 8). Accordingly, rotation of the spur gear 1008 (via actuation of the fourth drive input 906d) will control the feedbar and thereby control loading of surgical clips into the jaw members 610, 612 as desired.

The drive housing 608 further contains or houses fifth and sixth capstans 1002e and 1002f operatively coupled to or extending from the fifth and sixth drive inputs 906e,f (FIG. 9), respectively, such that actuation of the fifth and sixth drive inputs 906e,f results in rotation of the fifth and sixth capstans 1002e,f. The fifth and sixth capstans 1002e,f comprise capstan pulleys operatively coupled to the drive cables 808 (FIG. 8) such that rotation of a given capstan 1002e,f actuates (longitudinally moves) a corresponding one of the actuation cables 808. Accordingly, selective rotation of the fifth and sixth capstans 1002*e,f* via actuation of the fifth and sixth drive inputs 906*e,f*, respectively, will cause movement (axial translation) of the drive cables 808 and thereby articulate (pivot) the end effector 604 relative to the shaft 602.

The surgical tools 200, 600 described herein above may incorporate and facilitate the principles of the present disclosure in improving feeding and/or forming of surgical clips in robotic or non-robotic clip appliers. Moreover, it is contemplated herein to combine some or all of the features of the surgical tools 200, 600 to facilitate operation of the embodiments described below. Accordingly, example surgical tools that may incorporate the principles of the present disclosure may include geared actuators, capstan pulley and cable actuators, or any combination thereof, without departing from the scope of the disclosure.

Figure 11A:
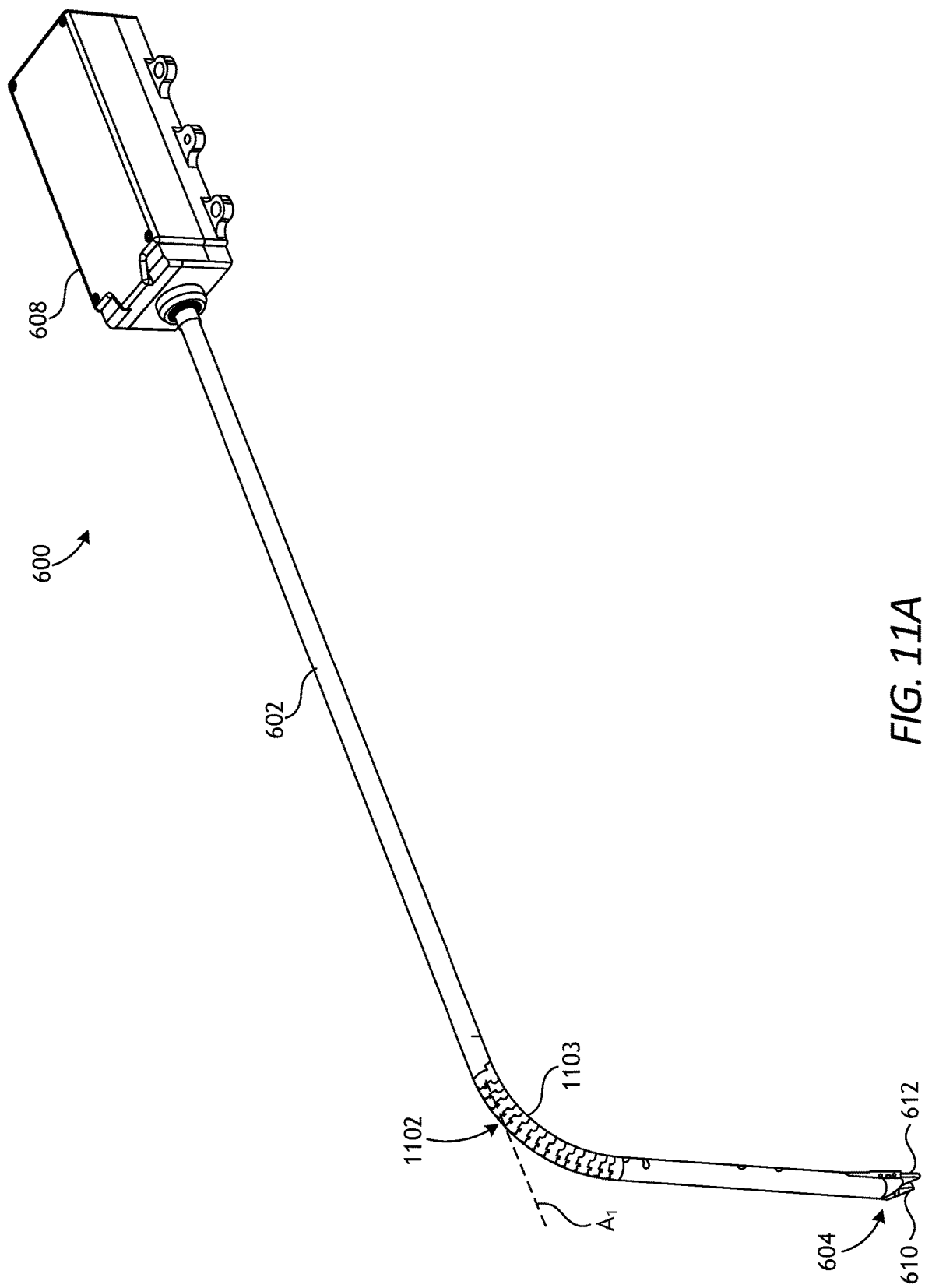
FIG. 11A is an isometric view of another example embodiment of the surgical tool of FIG. 6.

FIG. 11A is an isometric view of another example embodiment of the surgical tool 600, according to one or more additional embodiments. As illustrated, the articulation joint 606 of FIG. 6 is replaced with another articulation joint 1102. Similar to the articulation joint 600, the articulation joint 1102 couples the end effector 604 to the distal end of the shaft 602 and facilitates pivoting movement of the end effector 604 relative to the shaft 602 to position the end effector 604 at desired orientations and locations relative to a surgical site. In the illustrated depiction, the articulation joint 1102 has been moved (articulated) to redirect the end effector 604 off-axis relative to the longitudinal axis $A_1$ of the shaft 602.

Unlike the articulation joint 600 of FIG. 6, however, the articulation joint 1102 comprises a flexible shaft length 1103 and may be characterized or otherwise referred to as a "snake" shaft or "flex" shaft. More specifically, instead of incorporating rotatable axles and pulleys driven by drive cables, the articulation joint 1102 may comprise a flexible or movable shaft length 1103 interposing the end effector 604 and the shaft 602 and capable of articulating (pivoting) in one or more planes based on actuation input derived from the drive housing 608. Moreover, unlike the articulation joint 600, the articulation joint 1102 may provide or otherwise define a lumen that extends along its axial length and may be configured to house and/or convey surgical clips therethrough to be received at the end effector 604 for crimping. Accordingly, surgical clips can be stored within the articulation joint 1102 and/or proximal thereto and advanced distally through the articulation joint 1102 to be received between the jaw members 610, 612.

As used herein, the phrase "flexible shaft length" refers to the elongate body of an end effector articulation joint that is capable of bending or flexing between unarticulated and articulated states and that provides an inner lumen capable of storing surgical clips and/or facilitating distal advancement of surgical clips therethrough. While typical articulation joints have a fixed pivot or center of rotation, the flexible shaft length has a moving center of rotation. In one embodiment, for example, the flexible shaft length 1103 may comprise a series of articulation links rotatably coupled to each other and manipulatable with one or more drive cables extending from the drive housing 608. In such embodiments, selective actuation of the drive cable(s) causes the flexible shaft length 1103 to articulate (pivot) in one or more planes. In other embodiments, the flexible shaft length 1103 may comprise an elongate structure having a plurality of recesses removed along its length to enable the elongate structure to bend or flex in one or more planes upon assuming tensile loads derived from drive cable(s) extending from the drive housing 608. In yet other embodiments, the flexible shaft length 1103 may comprise a flexible or bendable shaft section capable of bending or flexing in one or more planes upon assuming tensile loads derived from drive cable(s) extending from the drive housing 608.

FIG. 11B is an exploded view of an example embodiment of the articulation joint 1102, according to one or more embodiments. While the articulation joint 1102 is described herein with respect to a particular snake shaft or flex shaft design, it will be appreciated that the articulation joint 1102 may alternatively comprise other snake shaft or flex shaft designs without departing from the scope of the disclosure. For example, suitable alternative forms of the articulation joint 1102 are described in U.S. Pat. No. 9,232,979 to Parihar et al., U.S. Pat. No. 8,685,020 to Weizman et al., U.S. Pat. No. 8,262,563 to Bakos et al., U.S. Pat. No. 8,403,945 to Whitfield et al., and U.S. Patent Pub. 2007/0084897 to Shelton, I V et al., the contents of which are hereby incorporated by reference.

As illustrated, the articulation joint 1102 may include a distal connector 1104*a*, a proximal connector 1104*b*, and a plurality of articulation links 1106 capable of being interconnected to extend between the distal and proximal connectors 1104*a,b*. The distal connector 1104*a* may be configured to couple the articulation joint 1102 to the end effector 604 (FIG. 11A), and the proximal connector 1104*b* may be configured to couple the articulation joint 1102 to the distal end of the shaft 602 (FIG. 11A). While FIG. 11B depicts fourteen articulation links 1106, the articulation joint 1102 could alternatively include more or less than fourteen articulation links 1106, without departing from the scope of the disclosure.

The articulation links 1106 are interconnectable in series to cooperatively form the flexible shaft length 1103. To accomplish this, each articulation link 1106 may provide or otherwise define a pair of lobes 1108 at one axial end and a corresponding pair of recesses 1110 at the opposite axial end. To interconnect the articulation links 1106, the lobes 1108 of the more proximal articulation links 1106 are received within or at the recesses 1110 of the more distal articulation links 1106. It will be appreciated, however, that the articulation links 1106 may alternatively be arranged in reverse where the lobes 1108 of the more distal articulation links 1106 would be received within the recesses 1110 of the more proximal articulation links 1106, without departing from the scope of the disclosure. A mechanical fastener (not shown), such as a pin or the like, may be used to couple the adjacent articulation links 1106 at the intersection of the corresponding lobes and recesses 1108, 1110. The mechanical fastener may allow relative (but limited) rotational movement between the adjacent articulation links 1106 about an articulation axis $A_3$ defined through each pair of lobes 1108 as interconnected with a corresponding pair of recesses 1110.

The distal-most articulation link 1106*a* may be coupled to a proximal end 1112*a* of the distal connector 1104*a*, and the proximal-most articulation link 1106*b* may be coupled to the distal end 1112*b* of the proximal connector 1104*b*. More specifically, the lobes 1108 of the distal-most articulation link 1106*a* may be received into corresponding recesses 1114 (one visible) provided on the distal connector 1104*a*, and the recesses 1110 of the proximal-most articulation link 1106*b* may receive corresponding lobes 1116 provided by the proximal connector 1104*b*. Similar to the interconnection of the articulation links 1106, a mechanical fastener may be used to couple the distal-most articulation link 1106*a* to the distal connector 1104*a*, and couple the proximal-most articulation link 1106*b* to the proximal connector 1104*b*. The mechanical fastener may or may not allow relative movement (rotation) between the adjacent component parts.

The articulation joint 1102 also includes one or more articulation cables, shown as a first articulation cable 1118*a* and a second articulation cable 1118*b*. The articulation cables 1118*a,b* are actuatable to move the articulation joint 1102 in at least one plane of motion. The articulation cables 1118*a,b* extend from the drive housing 608 (FIG. 11A), where they may be operatively coupled to one or more drive inputs operable to facilitate longitudinal translation of the articulation cables 1118*a,b* and thereby cause articulation of the articulation joint 1102. The articulation cables 1118*a,b* may extend along the entire axial length of the articulation joint 1102 and may terminate at the distal connector 1104*a* with a pair of cable connectors 1120.

The articulation cables 1118*a,b* may be operatively coupled to some or all of the articulation links 1106 as they extend along the axial length of the articulation joint 1102. In some embodiments, for example, the articulation cables 1118*a,b* may be threaded to/through some or all of the articulation links 1106. More specifically, the articulation cables 1118*a,b* may pass through opposing cable paths 1122 provided on angularly opposite sides of each articulation link 1106. When the articulation joint 1102 is assembled, the cable paths 1122 of each articulation link 1106 may axially align such that the articulation cables 1118*a,b* can pass therethough in a relatively direct course. The articulation cables 1118*a,b* are not bound within the cable paths 1122, thereby allowing the articulation cables 1118*a,b* to axially translate relative to the articulation links 1106 during operation, which facilitates articulation of the articulation joint 1102 in at least one plane of motion.

Having the two articulation cables 1118*a,b* arranged on angularly opposite sides of the articulation links 1106 allows the articulation cables 1118*a,b* to move the articulation joint 1102 in a single plane of motion, such as left-to-right or "yaw" motion. For example, when the articulation joint 1102 is assembled as described above, providing tension (pulling) on the first articulation cable 1118*a* and simultaneously slackening the second articulation cable 1118*b* may result in the articulation joint 1102 articulating in a first direction $B_1$. In contrast, providing tension (pulling) on the second articulation cable 1118*b* and simultaneously slackening the first articulation cable 1118*a* may result in the articulation joint 1102 articulating in a second direction $B_2$, opposite the first direction $B_1$.

The articulation joint 1102 may also be configured to move in a second plane of motion; i.e., up-and-down or "pitch" motion. To accomplish this, the elongate shaft 602 (FIG. 11A) may first be rotated 90° about the longitudinal axis $A_1$, such as by rotating the helical drive gear 1004 and corresponding driven gear 1006 of FIG. 10. As will be appreciated, rotating the elongate shaft 602 about the longitudinal axis $A_1$ allows the articulation joint 1102 to be articulated in an unlimited number of planes.

In embodiments where the articulation joint 1102 does not include the articulation links 1106 coupled at corresponding lobes 1108 and recesses 1110, however, an additional two articulation cables (not shown) may be included in the articulation joint 1102 and angularly offset from the first and second articulation cables 1118*a,b* by 90° about the periphery of each articulation link 1106. Providing tension (pulling) on one of the additional articulation cables while simultaneously slackening the other of the additional articulation cables will articulate the articulation joint 1102 in pitch.

When interconnected, the articulation links 1106 provide or otherwise define a lumen that extends along the entire length of the articulation joint 1102. As described herein, a plurality of surgical clips 1124 may be arranged or arrangeable in series within the lumen to be fed distally toward the end effector 604 (FIG. 11A). As illustrated, the surgical clips 1124 may be arranged in series such that the legs 1126 of the more proximal surgical clips 1124 engage at or near the crown 1128 of the more distal surgical clips 1124. While the surgical clips 1124 are depicted as arranged with the legs 1126 leading the corresponding crowns 1128 in the distal direction, it is equally contemplated herein to have the surgical clips 1124 arranged in reverse order, where the crown 1128 of each surgical clip 1124 leads in the distal direction.

In some embodiments, a feedbar 1130 (alternately referred to as a "clip pusher") may be used to push the series of surgical clips 1124 through the lumen of the articulation joint 1102. The feedbar 1130 may extend from the drive housing 608 (FIG. 11A) where it may be operatively coupled to one or more drive inputs operable to facilitate longitudinal translation of the feedbar 1130. In such embodiments, the drive input(s) may be selectively actuated to advance the feedbar 1130 (and, therefore, the surgical clips 1124) a predetermined distance. In other embodiments, however, the feedbar 1130 may be operatively coupled to another type drive mechanism arranged proximal to the articulation joint 1102 but distal to the drive housing 608. The feedbar 1130 may be rigid enough to provide an axial load on the surgical clips 1124, but flexible enough such that the feedbar 1130 is able to flex or bend when the articulation joint 1102 articulates during operation.

In other embodiments, however, the feedbar 1130 may be omitted and the surgical clips 1124 may instead be advanced through the articulation joint 1102 with another type of clip advancing device or mechanism. For example, in at least one embodiment, a biasing device (e.g., a spring or spring loaded feeder shoe) may be incorporated into the articulation joint 1102 to selectively advance the surgical clips 1124 toward the end effector 604 (FIG. 11A). In such embodiments, the biasing device may or may not have an indexible feeder shoe, as known in the art.

FIG. 11C is a cross-sectional side view of the assembled articulation joint 1102, according to one or more embodiments. As illustrated, the articulation links 1106 are interconnected and the articulation cables 1118*a,b* are operatively coupled to (e.g., threaded through) each articulation link 1106 and terminate at the distal connector 1104*a*, as generally described above. Moreover, the articulation joint 1102 is shown in a first or unarticulated state, where the articulation joint 1102 extends generally straight and otherwise coaxial with the longitudinal axis $A_1$ (FIGS. 6 and 11A) of the shaft 602.

As also illustrated, the assembled articulation links 1106 provide or otherwise cooperatively define a lumen 1132 that extends along the entire length of the articulation joint 1102. The surgical clips 1124 may be arranged in series within the lumen 1132 and the feedbar 1130 is positioned proximal to the surgical clips 1124 and poised to advance the surgical clips 1124 distally. In some embodiments, the surgical clips 1124 may be stored within the lumen 1132 until needed, but may alternatively be stored proximal to the articulation joint 1102 and advanced distally with the feedbar 1130 when needed.

In some embodiments, as illustrated, the articulation joint 1102 may further include a retention member 1134 positioned at or near the distal end of the articulation joint 1102.

In some embodiments, the retention member 1134 may be configured to engage the distal-most surgical clip 1124*a* and thereby prevent the serially-arranged (stacked) surgical clips 1124 from advancing distally until the axial load provided by the feedbar 1130 overcomes the retentive forces provided by the retention member 1134. Accordingly, the retention member 1134 may operate as an indexing mechanism to sequentially feed individual surgical clips 1124 to the end effector 604 (FIG. 11A).

In some embodiments, the retention member 1134 may comprise a passive biasing device, such as a gate spring or the like. In such embodiments, the spring force of the retention member 1134 may be sufficient to retain the stacked surgical clips 1124 in place, but may be overcome when the feedbar 1130 applies a sufficiently large axial load on the stacked surgical clips 1124. In other embodiments, however, the retention member 1134 may comprise an actuatable device configured to retain the stacked surgical clips 1124 in place and selectively release the distal-most surgical clip 1124*a* when actuated. In such embodiments, the retention member 1134 may be actuated and otherwise driven using any of the actuation components associated with the drive housings 206, 608 (FIGS. 2 and 6, respectively) discussed herein, or alternatively may be operatively coupled to a cable-driven worm gear or the like arranged near the articulation joint 1102.

In yet other embodiments, in addition to preventing the stacked surgical clips 1124 from advancing distally, or alternatively, the retention member 1134 may be configured to rotate the surgical clips 1124 to a predetermined orientation before the clips 1124 are fed into the end effector 604.

Figure 11D:
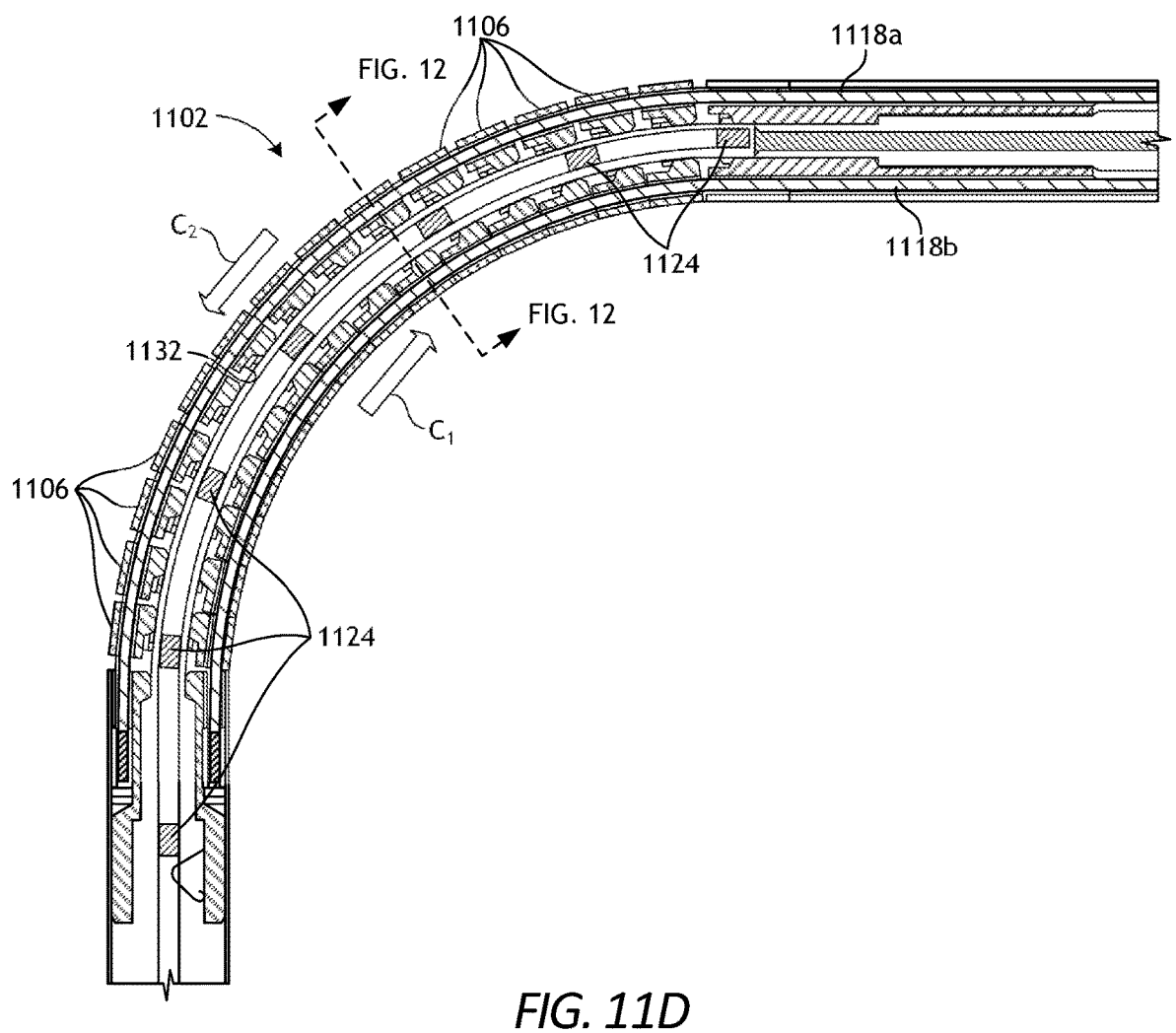
FIG. 11D is a cross-sectional side view of the assembled articulation joint of FIG. 11A in an articulated state.

FIG. 11D is another cross-sectional side view of the assembled articulation joint 1102, according to one or more embodiments. The articulation joint 1102 is shown in FIG. 11D as having moved from the unarticulated state of FIG. 11C to a second or articulated state. As used herein, "articulated state" refers to any position or orientation of the articulation joint 1102 that places the end effector 604 (FIG. 11A) off-axis from the longitudinal axis $A_1$ (FIG. 11A) of the shaft 602 (FIG. 11A). To transition the articulation joint 1102 to the depicted articulated state, a tensile load may be applied on the second articulation cable 1118*b* in the proximal direction $C_1$, while the first articulation cable 1118*a* is simultaneously slackened in the distal direction $C_2$. In contrast, to transition the articulation joint 1102 to an opposed articulated state in the same plane, a tensile load may be applied on the first articulation cable 1118*a* while simultaneously slackening the second articulation cable 1118*b*. The rotatably interconnected articulation links 1106 allow the articulated joint 1102 to flex (bend) as the articulation cables 118*a,b* are oppositely actuated.

Unlike conventional flex shaft designs and applications, the articulation joint 1102 may be capable of storing and/or conveying the surgical clips 1124 through the lumen 1132 defined by the articulation links 1106 while the articulation joint 1102 is in the unarticulated or articulated states. This advantage allows the surgical clips 1124 to be stored efficiently without interfering with the articulation joint 1102, and also allows for increased articulation with fine manipulation. The surgical clips 1124, however, must remain straight and otherwise non-deformed while the articulation joint 1102 articulates and/or as the surgical clips 1124 are fed distally through the articulation joint 1102. According to embodiments of the present disclosure, the articulation joint 1102 may provide or otherwise define a clip track configured to receive and guide the surgical clips 1124 through the articulation joint 1102. As described herein, the clip track may provide a pathway for the surgical clips 1124 to advance distally when the articulation joint is in the unarticulated or articulated states. When the articulation joint 1102 is in the articulated state, the clip track may be necessary to help guide the surgical clips 1124 through a tortuous path provided by the articulation joint 1102.

Figure 12:
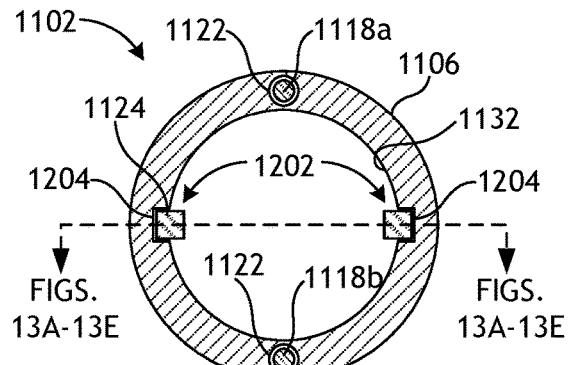
FIG. 12 is a cross-sectional end view of a portion of the articulation joint of FIGS. 11A-11D.

FIG. 12 is a cross-sectional end view of a portion of the articulation joint 1102, according to one or more embodiments. More specifically, FIG. 12 is a cross-sectional end view of an example articulation link 1106. In embodiments where the articulation joint 1102 does not include articulation links 1106, however, but instead comprises an elongate structure defining a plurality of recesses or comprises a flexible or bendable shaft section, FIG. 12 may depict a cross-sectional end view at any location along the axial length of the articulation joint 1102. For purposes of the present discussion, however, FIG. 12 will be described in conjunction with a cross-sectional end view of an example articulation link 1106. But it will be appreciated that the following description can equally be applied to alternative designs of the articulation joint 1102, without departing from the scope of the disclosure.

As illustrated, the articulation joint 1102 is generally cylindrical in shape and defines or otherwise provides the lumen 1132 that extends along the entire axial length of the articulation joint 1102. In other embodiments, however, the articulation joint 1102 may exhibit other cross-sectional shapes, such as polygonal (e.g., square) or ovoid, without departing from the scope of the disclosure. The first and second articulation cables 1118*a,b* are shown extending through corresponding cable paths 1122 located on angularly opposite positions of the articulation joint 1102. In other embodiments, the cable paths 1122 may be located external to the articulation joint 1102 and otherwise coupled to the exterior thereof, without departing from the scope of the disclosure.

A cross-sectional end view of an example surgical clip 1124 is also depicted in FIG. 12. In the illustrated embodiment, at least a portion of the surgical clip 1124 is received within a clip track 1202 defined in the inner wall of the lumen 1132. The clip track 1202 may be configured to support and guide the surgical clips 1124 within the lumen 1132 as they advance distally through the articulation joint 1102. Moreover, the clip track 1202 may help the surgical clips 1124 navigate through the single plane articulation joint 1102 by guiding the clips 1124 perpendicular to the bend direction. Consequently, the clip track 1202 helps align the surgical clips 1124 with the bend direction, which allows for higher curvature potential of the articulation joint 1102.

To accomplish this, the clip track 1202 may include opposing side rails 1204 (alternately referred to as "slots") defined on angularly opposite sides of the lumen 1132 and configured to receive and support corresponding portions of the surgical clips 1124. In some embodiments, as illustrated, the cross-sectional shape of the side rails 1204 may be polygonal (e.g., square or rectangular), but could alternatively be arcuate or ovoid in shape, without departing from the scope of the disclosure. In any event, the side rails 1204 may be shaped to receive and allow the surgical clips 1124 to slide therein as they advance distally within the lumen 1132.

In some embodiments, the clip track 1202 may twist or provide a helical path for the surgical clips 1124. In such embodiments, the surgical clips 1124 may enter the articulation joint 1102 in a vertical alignment, and the side rails 1204 may provide a helical path along the length of the articulation joint 1102 such that the surgical clips 1124 exit the articulation joint 1102 in a horizontal alignment. This may prove advantageous in embodiments where the jaw members 610, 612 (FIG. 11A) are horizontally-oriented, but the surgical clips 1124 are stored proximal to the end effector 604 (FIG. 11A) in a vertical orientation.

Figure 13A:
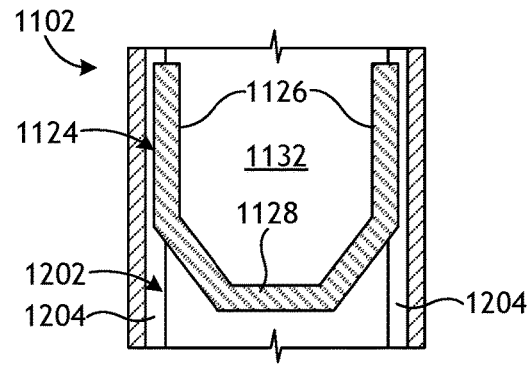
FIGS. 13A-13E are cross-sectional top views of the articulation joint of FIG. 12 taken along the indicated lines.

FIGS. 13A-13E are cross-sectional top views of the articulation joint 1102, as taken along the line indicated in FIG. 12. In FIG. 13A, the surgical clip 1124 is depicted within the lumen 1132 and supported by the clip track 1202. More specifically, the legs 1126 of the surgical clip 1124 are at least partially received into the opposing side rails 1204 and the crown 1128 is generally centered within the lumen 1132.

Figure 13B:
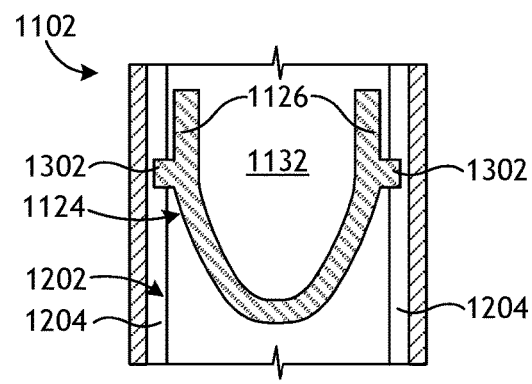

In FIG. 13B, the surgical clip 1124 includes or otherwise provides clip posts or tabs 1302 that extend laterally from each leg 1126. The clip tabs 1302 may be configured to extend into or otherwise be received within the opposing side rails 1204 of the clip track 1202. The clip tabs 1302 operate to support the surgical clip 1124 within the lumen 1132 and slidably engage the side rails 1204 as the surgical clip 1124 advances within the clip track 1202. At least one advantage to using surgical clips 1124 with the clip tabs 1302 is that the clips are more readily pivotable about the tabs, allowing for the highest attainable articulation of the clip without bending or pre-forming the clip in any way (as opposed to an entire length of a leg being captured in the curved track).

Figure 13C:
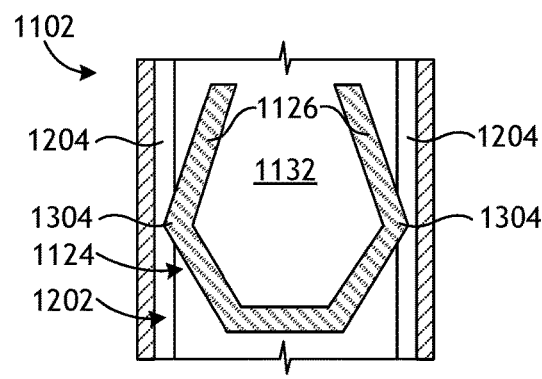

In FIG. 13C, the surgical clip 1124 is generally pear-shaped and has opposing shoulders 1304 defined on each leg 1126. The shoulders 1304 may comprise bends in the legs 1126 that are configured to extend into or otherwise be received within the opposing side rails 1204 of the clip track 1202. Similar to the clip tabs 1302 of FIG. 13B, the shoulders 1304 may operate to support the surgical clip 1124 within the lumen 1132 and slidably engage the side rails 1204 as the surgical clip 1124 advances within the clip track 1202.

In some embodiments, the surgical clip 1124 is received within the clip track 1202 via an interference fit that elastically flexes the legs inward and results in the surgical clip 1124 assuming the pear-shaped configuration. Upon exiting the confines of the lumen 1302, the legs 1126 may be able to flex and open fully. In other embodiments, however, the surgical clip 1124 may be naturally in the pear-shaped configuration. In such embodiments, the articulation joint 1102 may include a device or mechanism configured to receive the pear-shaped surgical clips 1124 from the lumen 1132 and re-form it to a shape ready for crimping. At least one advantage to using pear-shaped surgical clips 1124 is minimizing the diameter of the lumen 1132, which can minimize the size (diameter) of the end effector 604 (FIG. 11A). Moreover, the pear-shaped clips 1124 may also prove advantageous in providing small and tight packing (stacking).

Figure 13D:
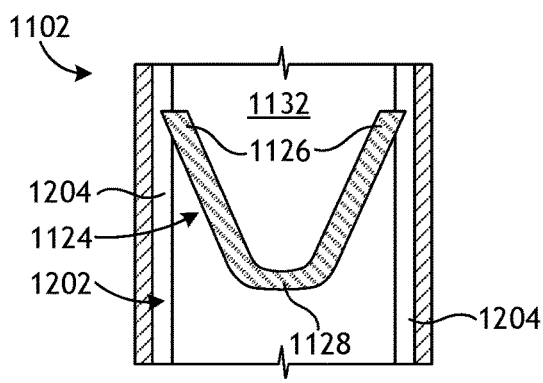

In FIG. 13D, the surgical clip 1124 is generally V-shaped and the legs 1126 may be angled toward the inner wall of the lumen 1132. The legs 1126 extend into and are otherwise received by the opposing side rails 1204 of the clip track 1202, and the angled legs 1126 operate to support the surgical clip 1124 within the lumen 1132 and slidably engage the corresponding side rails 1204 as the surgical clip 1124 advances distally within the articulation joint 1102.

At least one advantage to the V-shaped surgical clips 1124 is the ability to stack the surgical clips 1124 in a nested arrangement where the legs 1126 of the more proximal surgical clips 1124 extend past the crown 1128 of the more distal-surgical clips 1124. This nested arrangement allows more surgical clips 1124 to be stacked together in contrast to typical clip stacking arrangements where the legs 1126 of the more proximal surgical clips 1124 engage the crown 1128 of the more distal-surgical clips 1124.

Figure 13E:
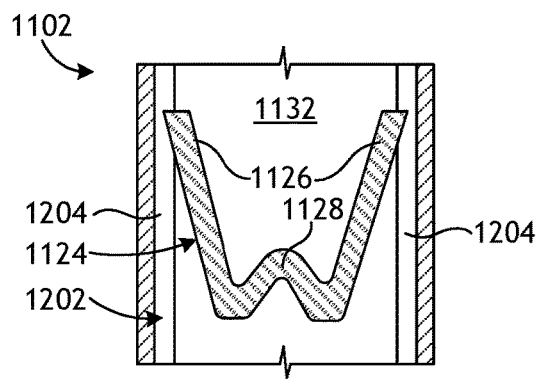

In FIG. 13E, the surgical clip 1124 is generally W-shaped. The legs 1126 may be angled toward the inner wall of the lumen 1132, and the crown 1128 may provide an undulating section. The legs 1126 extend into and are otherwise received by the opposing side rails 1204 of the clip track 1202. The angled legs 1126 operate to support the surgical clip 1124 within the lumen 1132 and slidably engage the corresponding side rails 1204 as the surgical clip 1124 advances distally within the articulation joint 1102. At least one advantage to the W-shaped surgical clip 1124 is that the undulating crown 1128 provides additional surfaces and/or structure to engage with the feedbar 1130 (FIG. 11B). In addition, the W-shaped surgical clip 1124 provides a similar ability to stack in a nested arrangement as the V-shaped clip 1128 of FIG. 13D, thus allowing more surgical clips to be stacked together.

Figure 14A:
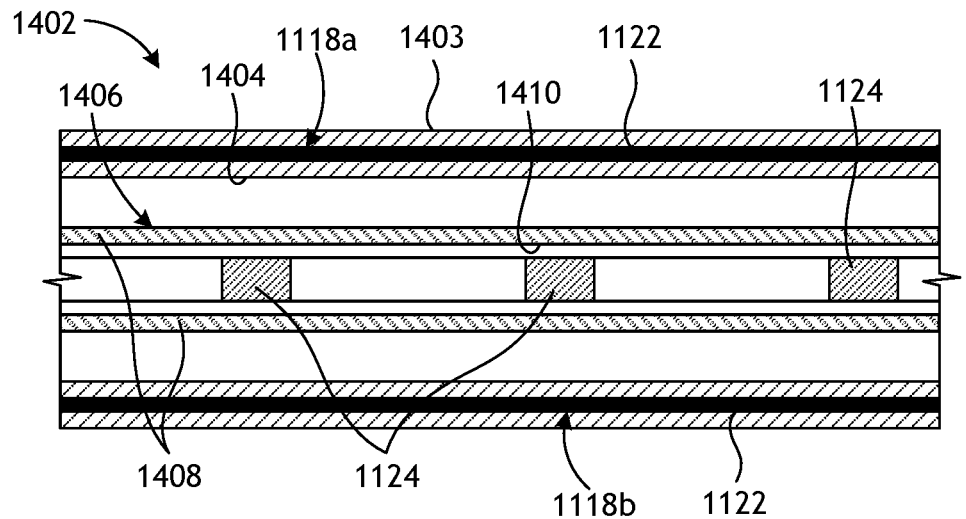
FIG. 14A is a cross-sectional side view of another example articulation joint.

FIG. 14A is a cross-sectional side view of another example articulation joint 1402, according to one or more embodiments of the present disclosure. The articulation joint 1402 may be similar in some respects to the articulation joint 1102 of FIGS. 11A-11D and, therefore, may be best understood with reference thereto. Similar to the articulation joint 1102, for example, the articulation joint 1402 may comprise a flexible shaft length 1403 that defines a lumen 1404 extending along the axial length of the articulation joint 1402. The lumen 1404 may be configured to house and/or convey a plurality of surgical clips 1124 therethrough to be received at the end effector 604 (FIG. 11A) for crimping. Accordingly, surgical clips 1124 can be stored within the flexible shaft length 1403 and/or proximal thereto and advanced distally through the articulation joint 1402 to be received between the jaw members 610, 612 (FIG. 11A).

Moreover, similar to the articulation joint 1102 of FIGS. 11A-11D, the articulation joint 1402 may include the articulation cables 1118a,b operatively coupled to the flexible shaft length 1403 to cause articulation thereof in at least one plane of motion. In the illustrated embodiment, the articulation cables 1118a,b are located on angularly opposite positions of the flexible shaft length 1403 (e.g., 180° offset) and extend along all or a portion of the axial length thereof. In some embodiments, the articulation cables 1118a,b may extend through the sidewall of the flexible shaft length 1403. More specifically, the articulation cables 1118a,b may be threaded through corresponding and opposing cable paths 1122 formed or otherwise provided on angularly opposite sides of the flexible shaft length 1403. In other embodiments, however, the articulation cables 1118a,b may be operatively coupled to the exterior of the flexible shaft length 1403. In such embodiments, the cable paths 1122 may be located external to the flexible shaft length 1403 and otherwise coupled to the exterior thereof.

The articulation cables 1118a,b may or may not be bound within the cable paths 1122. Moreover, in some embodiments, more than the two depicted articulation cables 1118a,b may be employed to allow the articulation joint 1402 to articulate in multiple planes of motion.

Unlike the articulation joint 1102 of FIGS. 11A-11D, however, the articulation joint 1402 may be made of a flexible material that allows the articulation joint 1402 to transition between unarticulated and articulated states in one or more planes of motion as acted upon by the articulation cables 1118a,b. Suitable flexible materials include, but are not limited to, a rubber (e.g., silicone rubber), a flexible plastic, an elastomer, nylon, spandex/lycra, and any combination thereof. In other embodiments, the flexible material may comprise a laser cut metal tube (that is one piece), which can flex like lower modulus materials. In yet other embodiments, the flexible material may comprise a woven metal or plastic sheath or jacketing.

The articulation joint 1402 may further provide or otherwise define a clip track 1406 configured to receive and guide the surgical clips 1124 through the lumen 1404. The clip track 1406 may provide a pathway for the surgical clips 1124 when the articulation joint 1402 is in the unarticulated or articulated states. When the articulation joint 1402 is in the articulated state, the clip track 1406 may be necessary to help guide the surgical clips 1124 through a tortuous path provided by the articulation joint 1402. Accordingly, the clip track 1406 may prove advantageous in helping the surgical clips 1124 navigate through the single plane articulation joint 1402 by guiding the clips 1124 perpendicular to the bend direction.

In the illustrated embodiment, the clip track 1406 comprises opposing guide rails 1408 arranged within the lumen 1404. The guide rails 1408 may be offset from each other and otherwise cooperatively define a clip passageway 1410 configured to receive and guide the surgical clips 1124 therein as they traverse the articulation joint 1402. As illustrated, the surgical clips 1124 are arranged in series within the clip passageway 1410. In some embodiments, the guide rails 1408 may be attached to the inner wall of the lumen 1404 at one or more locations. The number of attachment points may directly correlate to the flexibility of the guide rails 1408 relative to the lumen 1404 (e.g., more contact points=less flex, less contact points=more flex). In other embodiments, the guide rails 1408 may be attached at the proximal and distal ends of the articulation joint 1402.

The guide rails 1408 may be made of a flexible material, such as any of the flexible materials mentioned herein. This allows the clip track 1406 to correspondingly flex in response to movement (articulation) of the flexible shaft length 1403. The guide rails 1408 may be positioned within the lumen 1404 such that the clip passageway 1410 widens within a single plane to allow the surgical clips to align with the bend direction of the articulation joint 1402. Moreover, the guide rails 1408 may be positioned within the lumen 1404 such that the clip passageway 1410 becomes progressively wider near the point of maximum bend, such that the surgical clips 1124 are then capable of translating and rotating around said bend without binding at their distal or proximal ends.

The articulation joint 1102 is shown in FIG. 14A in a first or unarticulated state, where the articulation joint 1402 extends generally straight and otherwise coaxial with the longitudinal axis $A_1$ (FIGS. 6 and 11A) of the shaft 602.

Figure 14B:
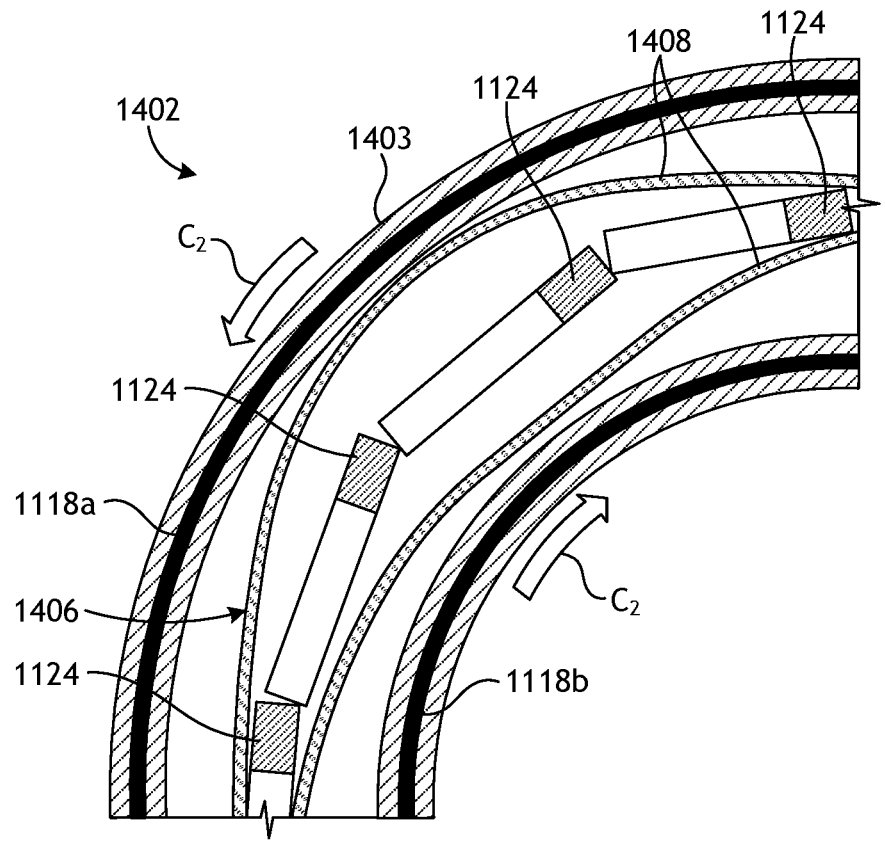
FIG. 14B is a cross-sectional side view of the articulation joint of FIG. 14B in an articulated state.

FIG. 14B is another cross-sectional side view of the articulation joint 1402, according to one or more embodiments. The articulation joint 1402 is shown in FIG. 14B as having moved from the unarticulated state of FIG. 14A to a second or articulated state. To transition the articulation joint 1402 to the depicted articulated state, a tensile load may be applied on the second articulation cable 1118b in the proximal direction $C_1$, while the first articulation cable 1118a is simultaneously slackened in the distal direction $C_2$. In contrast, to transition the articulation joint 1402 to an opposed articulated state in the same plane, a tensile load may be applied on the first articulation cable 1118a while simultaneously slackening the second articulation cable 1118b. The flexible material allows the articulated joint 1402 to flex (bend) as the articulation cables 118a,b are oppositely actuated.

As the articulation joint 1402 is moved to the articulated position, the guide rails 1408 flex and widen within a single plane perpendicular to the bend direction of the articulation joint 1402. As illustrated, the size of the clip passageway joint 1410 increases to accommodate the bend in the flexible shaft length 1403 and also to accommodate the axially-extending surgical clips 1124 as they traverse the tortuous path resulting from movement of the flexible shaft length 1403. As will be appreciated, this may prove advantageous in allowing the surgical clips 1124 to be fed distally within the clip track 1406 when the articulated joint 1402 is articulated in either direction. Moreover, the clip track 1406 helps align the surgical clips 1124 with the bend direction, which allows for higher curvature potential of the articulation joint 1402.

Figure 15A:
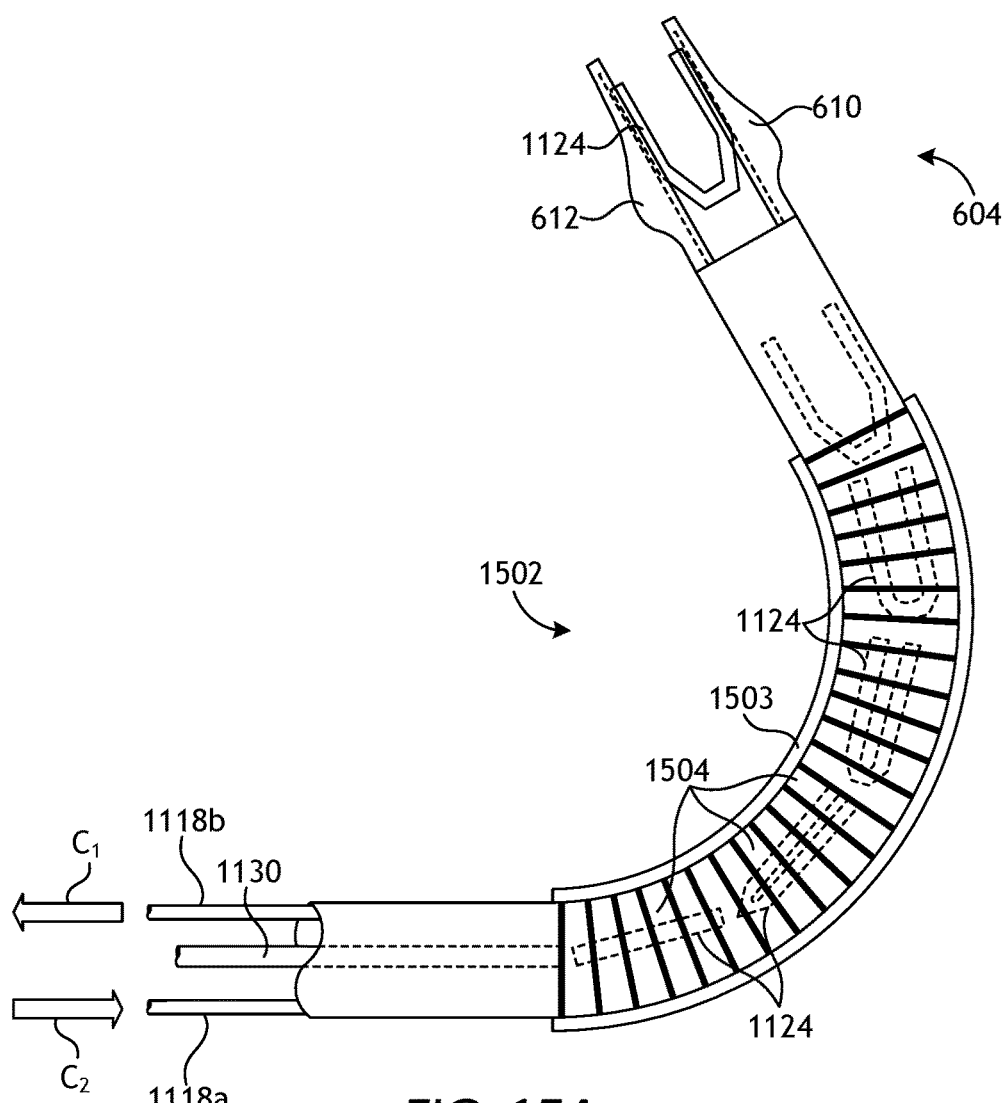
FIG. 15A is a side view of another example articulation joint.

FIG. 15A is a side view of another example articulation joint 1502, according to one or more embodiments of the present disclosure. The articulation joint 1502 may be similar in some respects to the articulation joints 1102 and 1402 of FIGS. 11A-11D and 14A-14B, respectively and, therefore, may be best understood with reference thereto. Similar to the articulation joints 1102 and 1402, for example, the articulation joint 1502 may comprise a flexible shaft length 1503 that defines a lumen that extends along its axial length. A plurality of surgical clips 1124 may be housed within and/or conveyed through the lumen to be received at the end effector 604 for crimping. Accordingly, surgical clips 1124 can be stored within the flexible shaft length 1503 and/or proximal thereto and advanced distally through the articulation joint 1502 with the feedbar 1130 to be received between the jaw members 610, 612.

Similar to the articulation joint 1102 of FIGS. 11A-11D, the articulation joint 1502 may include a plurality of articulation links 1504 that may be interconnectable in series to cooperatively form the flexible shaft length 1503. In other embodiments, however, the flexible shaft length 1503 may alternatively comprise a continuous shaft length made of a flexible material.

Furthermore, similar to the articulation joint 1102 and 1402 of FIGS. 11A-11D and 14A-14B, respectively, the articulation joint 1502 may include the articulation cables 1118a,b operatively coupled to the flexible shaft length 1503 to cause bending or flexing articulation thereof. In the illustrated embodiment, the articulation cables 1118a,b are located on angularly opposite sides of the flexible shaft length 1503 and extend along all or a portion of the axial length thereof. In some embodiments, the articulation cables 1118a,b may extend through the articulation links 1504, such as being threaded through each articulation link 1504 in corresponding cable paths (e.g., the cable paths 1122 of FIG. 11A).

To transition the articulation joint 1502 to the depicted articulated state, a tensile load may be applied on the second articulation cable 1118b in the proximal direction $C_1$, while the first articulation cable 1118a is simultaneously slackened in the distal direction $C_2$. In contrast, to transition the articulation joint 1502 to an opposed articulated state in the same plane, a tensile load may be applied on the first articulation cable 1118a while simultaneously slackening the second articulation cable 1118b.

The articulation joint 1502 may further include a clip track provided or otherwise defined within the lumen that helps guide the surgical clips 1124 toward the end effector 604. In the present embodiment, the clip track may be configured to twist or provide a helical path for the surgical clips 1124 to traverse along at least a portion of the articulation joint 1502. In some embodiments, for example, the surgical clips 1124 may enter the articulation joint 1502 in a vertical orientation and the clip track may provide a helical path that alters the orientation of the surgical clips 1124 such that the surgical clips 1124 exit the articulation joint 1502 in a horizontal alignment. Accordingly, the clip track may be configured to receive surgical clips 1124 in a first angular orientation, and discharge the surgical clips in a second angular orientation, where the second angular orientation is 90° offset from the first angular orientation. As will be appreciated, this may prove advantageous in applications where the surgical clips 1124 are stored in a vertical orientation, but the jaw members 610, 612 are arranged in a horizontal orientation. In such applications, the clip track may properly orient the surgical clips 1124 to be aligned with the jaw members 610, 612.

Figure 15B:
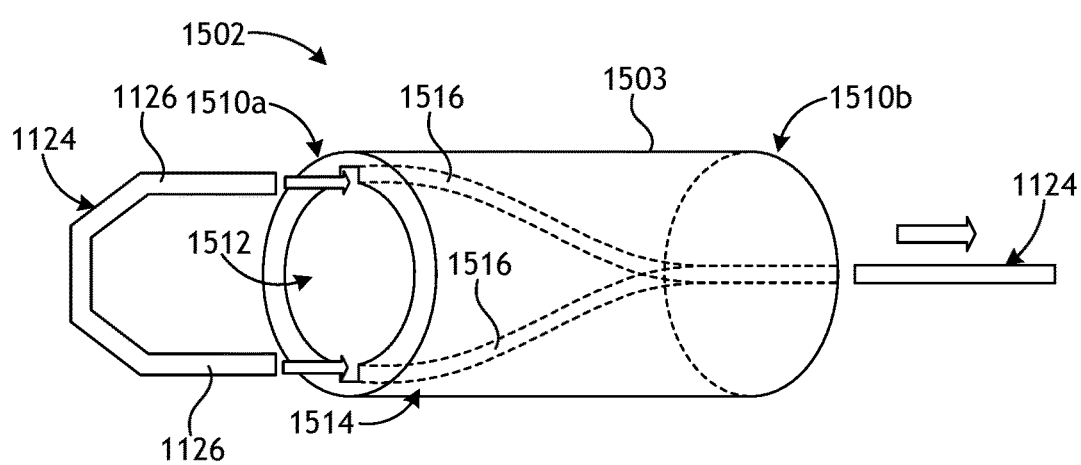
FIG. 15B is a shortened side view of at least a portion of the articulation joint of FIG. 15A.

FIG. 15B is a shortened side view of at least a portion of the articulation joint 1502 of FIG. 15A, according to one or more embodiments of the present disclosure. It is noted that the entire axial length of the articulation joint 1502 is not drawn to scale in FIG. 15B. Rather, for simplicity the length has been shortened for the present discussion.

As illustrated, the flexible shaft length 1503 comprises a generally cylindrical body having a proximal end 1510a and a distal end 1510b opposite the proximal end 1510a. In some embodiments, the flexible shaft length 1503 may comprise the interconnected articulation links 1504 of FIG. 15A, but could alternatively comprise a continuous shaft length made of a flexible material, as mentioned above. A lumen 1512 may be defined within the flexible shaft length 1503 and extends between the proximal and distal ends 1510a,b.

A clip track 1514 may be provided or otherwise defined by the articulation joint 1502 within the lumen 1512 and may extend between the proximal and distal ends 1510a,b. The clip track 1514 may be defined into the inner wall of the flexible shaft length 1503 and may comprise opposing side rails 1516 sized to receive a portion of the surgical clips 1124. For example, in some embodiments, the side rails 1516 may be configured to receive the legs 1126 of the surgical clips 1124. However, any of the configurations shown and described with reference to FIGS. 13A-13E may equally apply to this embodiment.

The side rails 1516 may extend distally in a corresponding curved or helical pathway between the proximal and distal ends 1510a,b. The helical pathway may be configured to transition the orientation of the surgical clips 1124 90° as they traverse the articulation joint 1502. Accordingly, a surgical clip 1124 oriented entering the articulation joint 1502 in a vertical orientation at the proximal end 1510a will be transitioned to a horizontal orientation upon traversing the clip track 1514 and exiting the articulation joint 1502 at the distal end 1510b.

In some embodiments, the clip track 1514 may be defined along only a portion of the flexible shaft length 1503. In such embodiments, the surgical clips 1124 may be conveyed at least partially through the flexible shaft length 1503 until encountering the clip track 1514. The surgical clips 1124 may then be fed into the clip track 1514 in a first angular orientation, and exit the clip track 1514 at a second angular orientation that is 90° offset from the first angular orientation. In other embodiments, however, the clip track 1514 may alternatively be provided by an entirely separate structure arranged distal to the articulation joint 1502, without departing from the scope of the disclosure.

Embodiments disclosed herein include:

A. A surgical clip applier that includes a drive housing, an elongate shaft that extends distally from the drive housing, an end effector arranged at a distal end of the elongate shaft and including first and second jaw members, and an articulation joint interposing the end effector and the elongate shaft. The articulation joint includes a flexible shaft length articulable in a plane of motion and having a first end and a second end, a lumen defined within the flexible shaft length and extending between the first and second ends, and a clip track provided within the lumen and extending at least partially between the first and second ends to guide surgical clips through the articulation joint to be received by the first and second jaw members for crimping.

B. A method of operating a surgical clip applier that includes positioning the surgical clip applier adjacent a patient for operation, the surgical clip applier including a drive housing, an elongate shaft that extends distally from the drive housing, an end effector arranged at a distal end of the elongate shaft and including first and second jaw members, and an articulation joint interposing the end effector and the elongate shaft. The articulation joint includes a flexible shaft length articulable in a plane of motion and having a first end and a second end, a lumen defined within the flexible shaft length and extending between the first and second ends, and a clip track provided within the lumen and extending at least partially between the first and second ends. The method further includes articulating the flexible shaft length in the plane of motion between an unarticulated state and an articulated state, advancing one or more surgical clips through the lumen with the flexible shaft length in the unarticulated state or the articulated state, guiding the one or more surgical clips through the articulation joint with the clip track, receiving a distal-most surgical clip of the one or more surgical clips from the articulation joint with the first and second jaw members, and collapsing the first and second jaw members to crimp the distal-most surgical clip.

Each of embodiments A and B may have one or more of the following additional elements in any combination: Element 1: wherein the clip track extends perpendicular to the plane of motion. Element 2: wherein the clip track provides opposing side rails defined on angularly opposite sides of the lumen and a portion of each surgical clip is receivable within and supported by the opposing side rails. Element 3: wherein the portion of each surgical clip slidably engages the opposing side rails as each surgical clip advances distally within the clip track. Element 4: wherein the clip track provides a helical path such that the surgical clips enter the flexible shaft length joint in a first angular orientation and exit the articulation joint in a second angular orientation angularly offset from the first angular orientation. Element 5: further comprising one or more articulation cables extending from the drive housing and operatively coupled to the flexible shaft length, wherein the one or more articulation cables are actuatable to move the articulation joint in the plane of motion. Element 6: wherein the flexible shaft length comprises a plurality of articulation links interconnected in series and extending between the first and second ends, and wherein the plurality of articulation links cooperatively define the lumen. Element 7: wherein the flexible shaft length is made of a flexible material that allows the articulation joint to bend in the plane of motion. Element 8: further comprising a feedbar movable within the lumen to advance the surgical clips distally through the clip track. Element 9:

further comprising biasing device arrangeable within the lumen to advance the surgical clips distally through the clip track. Element 10: wherein the articulation joint further comprises a retention member arranged at or near the distal end of the flexible shaft length to index the surgical clips. Element 11: wherein the retention member comprises a passive biasing device. Element 12: wherein the flexible shaft length is articulable between an unarticulated state and an articulated state, and wherein the surgical clips traverse the articulation joint when the flexible shaft is in the unarticulated and articulated states. Element 13: wherein the clip track comprises opposing guide rails offset from each other to cooperatively define a clip passageway that receives and guides the surgical clips through the articulation joint. Element 14: wherein the opposing guide rails are made of a flexible material and a size of the clip passageway increases when the flexible shaft length articulates.

Element 15: wherein the clip track provides opposing side rails defined on angularly opposite sides of the lumen, and wherein guiding the one or more surgical clips through the articulation joint with the clip track comprises receiving a portion of each surgical clip within the opposing side rails. Element 16: further comprising slidably engaging the portion of each surgical clip within the opposing side rails as each surgical clip advances distally within the clip track. Element 17: wherein the clip track provides a helical path, the method further comprising introducing the one or more surgical clips into the flexible shaft length in a first angular orientation, and discharging the one or more surgical clips from the flexible shaft length in a second angular orientation angularly offset from the first angular orientation. Element 18: wherein advancing the one or more surgical clips through the lumen comprises advancing the one or more surgical clips distally through the clip track with a feedbar movable within the lumen. Element 19: wherein the clip track comprises opposing guide rails made of a flexible material and offset from each other to cooperatively define a clip passageway, and wherein guiding the one or more surgical clips through the articulation joint comprises receiving and guiding the one or more surgical clips through the clip passageway, and increasing a size of the clip passageway when the flexible shaft length articulates to the articulated state.

By way of non-limiting example, exemplary combinations applicable to A and B include: Element 2 with Element 3; Element 2 with Element 4; Element 10 with Element 11; Element 13 with Element 14; Element 15 with Element 16; and Element 15 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical clip applier, comprising:
a drive housing;
an elongate shaft extending distally from the drive housing; and
an end effector arranged at a distal end of the shaft and including first and second jaw members, a cam slidably engageable with the first and second jaw members, and an actuation cable extending from the drive housing and operatively coupled to the cam; and
an articulation joint interposing the end effector and the shaft and including a distal clevis coupled to the end effector, a proximal clevis coupled to a distal end of the shaft, and a spacer interposing the distal and proximal clevises,
wherein the actuation cable extends through the articulation joint and wherein longitudinal movement of the actuation cable through the articulation joint moves the cam distally to collapse the first and jaw members.

2. The surgical clip applier of claim 1, wherein the end effector further comprises a pulley that receives and redirects the actuation cable for coupling with the cam.

3. The surgical clip applier of claim 1, wherein the actuation cable comprises a first actuation cable and the end effector further comprises a second actuation cable extending from the drive housing and operatively coupled to the cam,
wherein longitudinal movement of the first actuation cable moves the cam distally to collapse the first and second jaw members, and
wherein longitudinal movement of the second actuation cable moves the cam proximally and allows the first and second jaw members to open.

4. The surgical clip applier of claim 3, wherein a camming channel is defined in the cam and slidably receives cam tracks provided by the first and second jaw members, and wherein the camming channel pushes the first and jaw members together via the cam tracks as the cam is advanced distally.

5. The surgical clip applier of claim 1, wherein the spacer is rotatably coupled to the distal clevis at a first axle, and rotatably coupled to the proximal clevis at a second axle.

6. The surgical clip applier of claim 5, wherein a first pivot axis extends through the first axle and a second pivot axis extends through the second axle and is perpendicular to first pivot axis.

7. The surgical clip applier of claim 1, further comprising a plurality of drive cables extending through the articulation joint and operatively coupled to the end effector, wherein selective actuation of the plurality of drive cables causes the end effector to articulate relative to the shaft.

8. The surgical clip applier of claim 1, wherein the distal clevis is pivotally coupled to the spacer about a first pivot axis, and wherein the spacer is pivotally coupled to the proximal clevis about a distinct second pivot axis that is inclined with respect to the first pivot axis.

9. A method of operating a surgical clip applier, comprising:
positioning the surgical clip applier adjacent a patient for operation, the surgical clip applier including a drive housing, an elongate shaft extending distally from the drive housing, an articulation joint defined at a distal end of the shaft, and an end effector arranged at the distal end of the shaft and including:
first and second jaw members;
a cam slidably engageable with the first and second jaw members; and
an actuation cable extending from the drive housing through the articulation joint and operatively coupled to the cam,
actuating the actuation cable from the drive housing and thereby longitudinally moving the actuation cable;
moving the cam distally and toward the first and second jaw members with the actuation cable; and
collapsing the first and second jaw members as the cam moves distally.

10. The method of claim 9, wherein collapsing the first and second jaw members comprises:
receiving a surgical clip between the first and second jaw members; and
crimping the surgical clip as the first and second jaw members collapse.

11. The method of claim 9, wherein the actuation cable comprises a first actuation cable and the end effector further comprises a second actuation cable extending from the drive housing and operatively coupled to the cam, the method further comprising:
longitudinally moving the first actuation cable and thereby advancing the cam distally to collapse the first and second jaw members;
longitudinally moving the second actuation cable and thereby moving the cam proximally; and
opening the first and second jaw members as the cam moves proximally.

12. The method of claim 9, wherein a camming channel is defined in the cam to slidably receive cam tracks provided by the first and second jaw members, the method further comprising pushing the first and jaw members together with the camming channel via the cam tracks as the cam is advanced distally.

13. The method of claim 12, wherein the articulation joint includes a distal clevis coupled to the end effector, a proximal clevis coupled to a distal end of the shaft, and a spacer interposing the distal and proximal clevises, the method further comprising:
rotatably coupling the spacer to the distal clevis at a first axle; and
rotatably coupling the spacer to the proximal clevis at a second axle orthogonal to the first axle.

14. The method of claim 13, where in the end effector further comprises a plurality of drive cables extending through the articulation joint and operatively coupled to the end effector, the method further comprising actuating the plurality of drive cables and thereby articulating the end effector relative to the shaft.

* * * * *